United States Patent
Kori et al.

(10) Patent No.: US 9,728,420 B2
(45) Date of Patent: Aug. 8, 2017

(54) ORGANIC FILM COMPOSITION, PROCESS FOR FORMING ORGANIC FILM, PATTERNING PROCESS, AND COMPOUND

(71) Applicant: SHIN-ETSU CHEMICAL CO., LTD., Tokyo (JP)

(72) Inventors: Daisuke Kori, Jyoetsu (JP); Kazumi Noda, Jyoetsu (JP); Kazunori Maeda, Jyoetsu (JP); Rie Kikuchi, Jyoetsu (JP); Tsutomu Ogihara, Jyoetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 15/091,336

(22) Filed: Apr. 5, 2016

(65) Prior Publication Data
US 2016/0336189 A1    Nov. 17, 2016

(30) Foreign Application Priority Data

May 14, 2015   (JP) ................... 2015-098795

(51) Int. Cl.
*H01L 21/31*      (2006.01)
*C07C 219/32*     (2006.01)
(Continued)

(52) U.S. Cl.
CPC .............. *H01L 21/31* (2013.01); *C07C 69/33* (2013.01); *C07C 69/76* (2013.01); *C07C 69/84* (2013.01);
(Continued)

(58) Field of Classification Search
CPC ............... H01L 21/31; H01L 21/31138; H01L 21/31058; H01L 21/31056; H01L 21/32;
(Continued)

(56) References Cited

U.S. PATENT DOCUMENTS 3,774,305 A * 11/1973 Stoffey ............... C08F 20/20
                                                 433/228.1
5,476,748 A * 12/1995 Steinmann ......... C08F 283/00
                                                 430/269
(Continued)

FOREIGN PATENT DOCUMENTS

EP    0 388 979 A2 *  9/1990
IN    003MU01114 A *  9/2005
(Continued)

OTHER PUBLICATIONS

Shakhashiri, "chemical of the Week: Gases of the air" Chemistry 103-1, www.scifun.org, Nov. 2007, two pages.*
(Continued)

*Primary Examiner* — Cynthia Hamilton
(74) *Attorney, Agent, or Firm* — Oliff PLC

(57) ABSTRACT

An organic film composition including a compound represented by the following general formula (1),

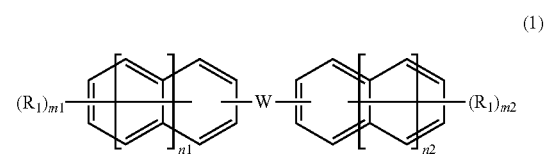

wherein n1 and n2 each independently represent 0 or 1; "W" represents a single bond or any of structures represented by the following formula (2); $R_1$ represents any of structures represented by the following general formula (3); m1 and m2 each independently represent an integer of 0 to 7, with the proviso that m1+m2 is 1 to 14.

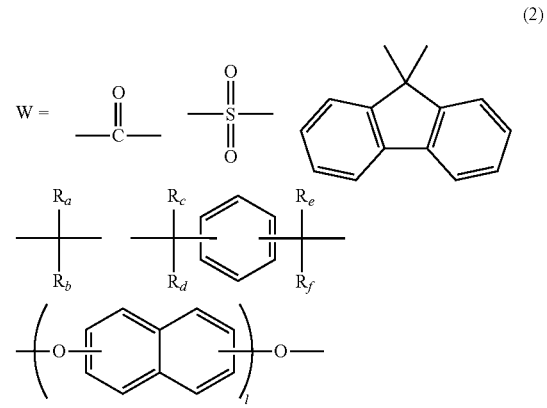

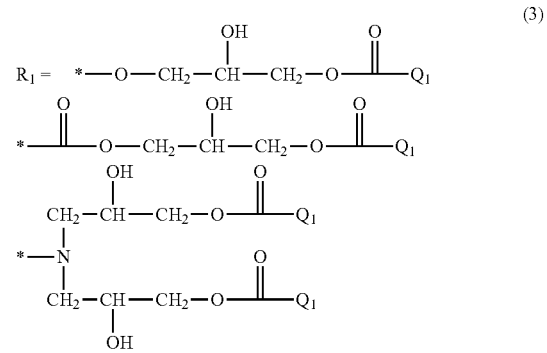

There can be provided an organic film composition for forming an organic film having dry etching resistance as well as advanced filling/planarizing characteristics.

15 Claims, 2 Drawing Sheets

(51) Int. Cl.
| | |
|---|---|
| *G03F 7/11* | (2006.01) |
| *C07C 69/94* | (2006.01) |
| *C07C 317/22* | (2006.01) |
| *C07C 69/84* | (2006.01) |
| *H01L 21/32* | (2006.01) |
| *H01L 21/324* | (2006.01) |
| *H01L 21/3105* | (2006.01) |
| *H01L 21/311* | (2006.01) |
| *C07C 69/33* | (2006.01) |
| *C07C 69/76* | (2006.01) |
| *C07C 219/14* | (2006.01) |
| *G03F 7/09* | (2006.01) |

(52) U.S. Cl.
CPC ............ *C07C 69/94* (2013.01); *C07C 219/14* (2013.01); *C07C 317/22* (2013.01); *G03F 7/091* (2013.01); *G03F 7/094* (2013.01); *H01L 21/31056* (2013.01); *H01L 21/31058* (2013.01); *H01L 21/31138* (2013.01); *H01L 21/31144* (2013.01); *H01L 21/32* (2013.01); *H01L 21/324* (2013.01); *C07C 2103/18* (2013.01); *C07C 2103/24* (2013.01)

(58) Field of Classification Search
CPC .. H01L 21/31144; H01L 21/324; G03F 7/091; G03F 7/094; C07C 69/33; C07C 219/14; C07C 69/76; C07C 69/84; C07C 317/22; C07C 69/94; C07C 2103/18; C07C 2103/24
See application file for complete search history.

(56) References Cited

U.S. PATENT DOCUMENTS

| | | | | |
|---|---|---|---|---|
| 6,534,621 B2* | 3/2003 | Boriack | ................. | C08G 59/00 525/507 |
| 2002/0106909 A1 | 8/2002 | Kato et al. | | |
| 2005/0255712 A1 | 11/2005 | Kato et al. | | |
| 2006/0019195 A1 | 1/2006 | Hatakeyama et al. | | |
| 2006/0204891 A1 | 9/2006 | Hatakeyama | | |
| 2007/0004228 A1* | 1/2007 | Hatanaka | ................. | G03F 7/091 438/780 |
| 2008/0318167 A1* | 12/2008 | Kim | ..................... | C09D 131/02 430/319 |
| 2009/0274978 A1 | 11/2009 | Ohashi et al. | | |
| 2009/0311624 A1 | 12/2009 | Horiguchi et al. | | |
| 2010/0099044 A1 | 4/2010 | Hatakeyama et al. | | |
| 2014/0170345 A1* | 6/2014 | Aoshima | ................. | C08J 7/045 428/35.4 |

FOREIGN PATENT DOCUMENTS

| | | | |
|---|---|---|---|
| JP | 2002-334869 A | | 11/2002 |
| JP | 2004-169198 a | * | 6/2004 |
| JP | 2004-205685 A | | 7/2004 |
| JP | 2005-128509 A | | 5/2005 |
| JP | 2005-250434 A | | 9/2005 |
| JP | 2006-227391 A | | 8/2006 |
| JP | 2006-285095 A | | 10/2006 |
| JP | 2006-293298 A | | 10/2006 |
| JP | 2007-199653 A | | 8/2007 |
| JP | 2008158002 A | | 7/2008 |
| JP | 2009-269953 A | | 11/2009 |
| JP | 2010-122656 A | | 6/2010 |
| JP | 2011-140637 a | * | 7/2011 |
| JP | 1784784 B2 | | 10/2011 |
| JP | 2012-206968 a | * | 10/2012 |
| WO | 2004/066377 A1 | | 8/2004 |
| WO | WO-2013/047523 a | * | 4/2013 |

OTHER PUBLICATIONS

He et al J. POlym Res (2012) nine pages. DOI 10.1007/s10965-012-9932-3.Published online: Jul. 14, 2012.*
English translation of JP, 2012-206968, A (2012) from machine translation from AIPN Japan Patent Office National Center for Industrial Property Information and Training, generated Jan. 6, 2017, 12 pages.*
English translation of JP, 2004-169198, A (2004) from machine translation from AIPN Japan Patent Office National Center for Industrial Property Information and Training, generated Jan. 6, 2017, 14 pages.*
Gawdzik et al, "Synthesis of Glycidyl Amine Adducts and Their Copolymerization with Glycidyl Methacrylate ", Journal of Applied Polymer Science, vol. 98, 2461-2466 (2005) Published online in Wiley InterScience (www.interscience.wiley.com).*
English translation of JP, 2011-1 40637 a, A (2011) from machine translation from AIPN Japan Patent Office National Center for Industrial Property Information and Training, generated Jan. 6, 2017, 15 pages.*

* cited by examiner (G)

(H)

(I)

(J)

(K)

ORGANIC FILM COMPOSITION, PROCESS FOR FORMING ORGANIC FILM, PATTERNING PROCESS, AND COMPOUND

BACKGROUND OF THE INVENTION

Field of the Invention

The present invention relates to a resist under layer film composition to be used in a multilayer resist step which is used for a fine processing in a manufacturing step of a semiconductor apparatus, etc., or an organic film composition effective for a planarizing composition for manufacturing a semiconductor apparatus, a process for forming a film using the same, a patterning process using the organic film composition suitable for exposure by using a far ultraviolet ray, a KrF excimer laser (248 nm), an ArF excimer laser (193 nm), an $F_2$ laser (157 nm), a $Kr_2$ laser (146 nm), an $Ar_2$ laser (126 nm), a soft X-ray (EUV), an electron beam (EB), an ion beam, an X-ray, or the like, and a compound useful as a component of the organic film composition.

Description of the Related Art

As an LSI advances toward higher integration and higher processing speed, miniaturization of pattern size is rapidly progressing. In accordance with this miniaturization, the lithography technology therein has achieved formation of a fine pattern by shifting the wavelength of a light source shorter and by proper selection of a resist composition for such a light source. The main stream of this is a positive photoresist composition used in a monolayer. In this monolayer positive photoresist composition, a resist mechanism is constructed such that a skeleton having an etching resistance to dry etching by a gas plasma of a chlorine type or a fluorine type is introduced into a resist resin, and that an exposed part thereof is dissolved, so that a pattern may be formed by dissolving the exposed part, and then a substrate to be processed which is coated with the resist composition may be dry etched by using the remained resist pattern as an etching mask.

However, if miniaturization is pursued without changing a film thickness of the photoresist film to be used, or in other words, if the pattern width thereof is made further smaller, the resolution performance of the photoresist film is lowered. And in addition, when the photoresist film is pattern-developed by a developer, a so-called aspect ratio thereof is so large that a phenomenon of the pattern collapse occurs. In view of the above-mentioned, film thickness of the photoresist film has been made thinner in accordance with this miniaturization.

On the other hand, for processing of a substrate to be processed, a method of processing this substrate by dry etching using a photoresist film having a formed pattern as an etching mask has been usually used. Practically, however, there is no dry etching method capable of providing a complete etching selectivity between the photoresist film and the substrate to be processed; and thus, during processing of the substrate, the resist film is also damaged and causes collapse of the resist film during the time of processing of the substrate so that the resist pattern cannot be transferred precisely to the substrate to be processed. Accordingly, the resist composition has been required to have a further higher dry etching resistance in accordance with finer patterning. Also, because of the shift of the exposure light to a shorter wavelength, a resin used for the photoresist composition is required to have a smaller light absorbance at the wavelength of the exposure light, so that, in accordance with the shift to i-beam, KrF, and ArF, the resin has been shifting to a novolac resin, polyhydroxystyrene, and a resin having an aliphatic polycyclic skeleton. Practically, however, the etching rate under the dry etching condition mentioned above is increasing so that recent photoresist compositions having a high resolution tend to have rather a lower etching resistance.

In the situation as mentioned above, a substrate to be processed must be dry etched by using a photoresist film having a thinner thickness and a lower etching resistance than ever; and thus, securement of a material in this process and a process itself has become imperative.

A multilayer resist process is one of solutions for these problems. This process is as follows: a middle layer film having a different etching selectivity from a photoresist film (that is, a resist upper layer film) is set between the resist upper layer film and a substrate to be processed, and then, to obtain a pattern on the resist upper layer film; the pattern is transferred to the middle layer film by dry etching by using the resist upper layer film pattern as a dry etching mask; and then the pattern is transferred to the substrate to be processed by dry etching by using the middle layer film as a dry etching mask.

The multilayer resist process further include a three-layer resist process which can be performed by using a typical resist composition used in a monolayer resist process. For example, this three-layer resist process is configured to form: an organic film based on novolac resin or the like as a resist under layer film on a substrate to be processed; a silicon-containing film as a resist middle layer film thereon; and a usual organic photoresist film as a resist upper layer film thereon. Since the organic resist upper layer film exhibits an excellent etching selectivity ratio relative to the silicon-containing resist middle layer film for dry etching by fluorine-based gas plasma, the resist upper layer film pattern is transferred to the silicon-containing resist middle layer film by means of dry etching based on fluorine-based gas plasma. Further, since the silicon-containing resist middle layer film exhibits an excellent etching selectivity ratio relative to an organic under layer film in the etching using an oxygen gas or a hydrogen gas, pattern of the silicon-containing middle layer film is transferred to the under layer film by means of etching based on an oxygen gas or a hydrogen gas. According to this process, even when a resist composition which is difficult to form a pattern having a sufficient film thickness for directly processing the substrate to be processed or a resist composition which has insufficient dry etching resistance for processing the substrate is used, pattern of the organic film (resist under layer film) of novolac resin and so on having a sufficient dry etching resistance for the processing can be obtained when the pattern can be transferred to the silicon-containing film (resist middle layer film).

While numerous materials have been known (for example, Patent Document 1) for the organic under layer film as described above, in recent years, it has now been growing necessity to have excellent filling and planarizing characteristics in addition to dry etching resistance. For example, when a ground substrate to be processed has a fine pattern structure such as a hole or a trench, it is necessary to have filling property which fills the pattern with a film without any voids. In addition, when the ground substrate to be processed has a step(s), or when a pattern dense portion and no pattern region exist on the same wafer, it is necessary to planarize the film surface by the under layer film. By planarizing the surface of the under layer film, fluctuation in the film thickness of a middle layer or a photoresist formed thereon is controlled, whereby a focus margin in lithography or a margin in the processing step of the substrate to be processed thereafter can be enlarged.

As a method of improving filling/planarizing characteristics of an under layer film composition, addition of a liquid state additive such as a polyether polyol has been proposed (Patent Document 2). However, the organic film formed by the method contains a large amount of the polyether polyol units, etching resistance of which are inferior, so that the etching resistance of the resulting film is markedly lowered whereby it is not suitable for an under layer film for the three-layer resist. Thus, it has been desired to develop a resist under layer film composition having both of excellent filling/planarizing characteristics and sufficient etching resistance, and a patterning process using the same.

Also, uses of an organic film composition excellent in filling/planarizing characteristics are not limited only to an under layer film for the three-layer resist, and it can be widely applied also as a planarizing composition for manufacturing a semiconductor apparatus, for example, planarizing a substrate prior to patterning by nano imprinting, etc. Moreover, for global planarizing during the manufacturing process of the semiconductor apparatus, a CMP process has now generally been used, but the CMP process is a high cost process, so that such a composition is expected to be a composition to serve the global planarizing method to be used in place of the CMP process.

PRIOR ART DOCUMENTS

Patent Documents

[Patent Document 1] Japanese Patent Laid-Open Publication No. 2004-205685
[Patent Document 2] Japanese Patent No. 4784784

SUMMARY OF THE INVENTION

The present invention has been done in view of the situation as mentioned and an object thereof is to provide an organic film composition for forming an organic film having dry etching resistance as well as advanced filling/planarizing characteristics.

In order to solve the problems, the present invention provides an organic film composition comprising a compound represented by the following general formula (1),

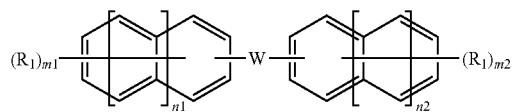

wherein n1 and n2 each independently represent 0 or 1; "W" represents a single bond or any of structures represented by the following formula (2); $R_1$ represents any of structures represented by the following general formula (3); m1 and m2 each independently represent an integer of 0 to 7, with the proviso that m1+m2 is 1 to 14;

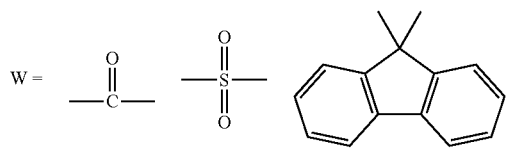

-continued wherein "l" represents an integer of 0 to 3; $R_a$ to $R_f$ each independently represent a hydrogen atom, or an alkyl group having 1 to 10 carbon atoms, a phenyl group, or a phenylethyl group which may be substituted by a fluorine atom, and $R_a$ and $R_b$ may be bonded to each other to form a ring compound;

wherein "*" represents a bonding site to the aromatic ring; $Q_1$ represents a linear or branched saturated or unsaturated hydrocarbon group having 1 to 30 carbon atoms, an alicyclic group having 4 to 20 carbon atoms, or a substituted or unsubstituted phenyl group, naphthyl group, anthracenyl group, or pyrenyl group, and the methylene group constituting $Q_1$ may be substituted by an oxygen atom or a carbonyl group when $Q_1$ represents a linear or branched saturated or unsaturated hydrocarbon group having 1 to 30 carbon atoms.

Such an organic film composition enables to form an organic film having both of high dry etching resistance and advanced filling/planarizing characteristics.

In this case, the compound represented by the general formula (1) is preferably a compound represented by the following general formula (4),

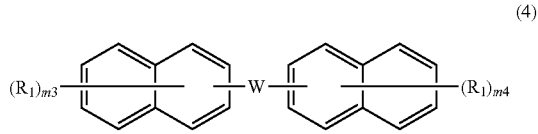

wherein m3 and m4 represent 1 or 2; and "W" and $R_1$ have the same meanings as defined above.

An organic film composition which contains a compound having such a naphthalene ring enables to give an organic film composition with excellent dry etching resistance and heat resistance.

In this case, "W" is preferably a single bond or any of structures represented by the following formula (5)

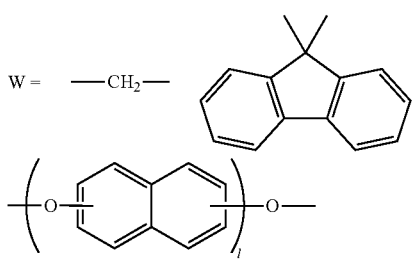

(5)

wherein "l" has the same meaning as defined above.

When "W" is such a structure, it is possible to give heat resistance and etching resistance without deteriorating filling/planarizing characteristics.

In this case, the compound represented by the general formula (1) preferably has two or more $Q_1$ in the molecule, and contains one or more structures represented by the following general formula (6) and one or more structures represented by the following general formula (7) respectively as $Q_1$.

(6)

wherein "**" represents a bonding site to the carbonyl group; $R_h$ represents a linear or branched saturated or unsaturated hydrocarbon group having 1 to 30 carbon atoms, and the methylene group constituting $R_h$ may be substituted by an oxygen atom or a carbonyl group,

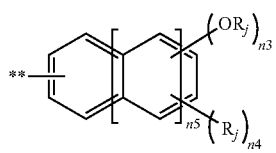

(7)

wherein "**" represents a bonding site to the carbonyl group; $R_i$ represents a hydrogen atom, or a linear or branched hydrocarbon group having 1 to 10 carbon atoms; $R_j$ represents a linear or branched hydrocarbon group having 1 to 10 carbon atoms, a halogen atom, a nitro group, an amino group, a nitrile group, an alkoxycarbonyl group having 1 to 10 carbon atoms, or an alkanoyloxy group having 1 to 10 carbon atoms; n3 and n4 represent the numbers of substituents on the aromatic ring, and each represent an integer of 0 to 7, with the proviso that n3+n4 is 0 to 7; n5 represents 0 to 2.

In the organic film composition which contains such a compound, it is possible to improve the filling/planarizing characteristics by enhancing thermal fluidity without deteriorating the heat resistance and etching resistance, and it is also possible to obtain an organic film composition in which the optical constants are controllable.

Preferably, the foregoing organic film composition further contains at least one of (A) an acid generator, (B) a cross-linking agent, (C) a surfactant, and (D) an organic solvent.

As described above, in the organic film composition of the present invention, it is possible to add (A) an acid generator and (B) a cross-linking agent to accelerate the cross-linking and curing reaction. It is also possible to add (C) a surfactant in order to improve the coating property in spin coating. In addition, the organic film composition changes to a solution by adding (D) an organic solvent, which can be spin coated.

The inventive organic film composition is preferably a one which is used as a resist under layer film composition or a planarizing composition for manufacturing a semiconductor apparatus.

By using the inventive organic film composition to form a multilayer resist film which is applied to a fine processing in the manufacturing step of a semiconductor apparatus and so on, it is possible to provide a resist under layer film composition for forming a resist under layer film having both of high dry etching resistance and high filling/planarizing characteristics. It is also possible to provide a planarizing composition for manufacturing a semiconductor apparatus with excellent filling/planarizing characteristics applicable to planarization in the manufacturing step of a semiconductor apparatus other than multilayer resist processes.

The present invention also provides a process for forming an organic film which is used as a resist under layer film of a multilayer resist film used in lithography or a planarizing film for manufacturing a semiconductor apparatus, comprising:

coating a substrate to be processed with the foregoing organic film composition, and subjecting the organic film composition to heat treatment at a temperature of 100° C. or higher and 600° C. or lower for 10 to 600 seconds to form a cured film.

Thus, by coating the organic film composition and subjecting the organic film composition to heat treatment at a temperature of 100° C. or higher and 600° C. or lower for 10 to 600 seconds whereby the cross-linking reaction can be accelerated and mixing with the upper layer film can be prevented.

The present invention also provides a process for forming an organic film which is used as a resist under layer film of a multilayer resist film used in lithography or a planarizing film for manufacturing a semiconductor apparatus, comprising:

coating a substrate to be processed with the foregoing organic film composition, and baking the organic film composition under an atmosphere with an oxygen concentration of 0.1% or more and 21% or less to form a cured film.

By baking the inventive organic film composition under such an oxygen atmosphere, a sufficiently cured organic film can be obtained.

In this case, it is also preferable to use a substrate having a structure or step(s) each with a height of 30 nm or more as the substrate to be processed.

The inventive organic film composition is excellent in filling/planarizing characteristics, so that it is particularly useful for forming a planarizing organic film on the substrate having a structure or step(s) each with a height of 30 nm or more.

The present invention also provides a patterning process which is a process for forming a pattern on a substrate to be processed, comprising at least the steps of:

forming a resist under layer film on the substrate to be processed by using the foregoing organic film composition;

forming a resist middle layer film on the resist under layer film by using a resist middle layer film composition containing a silicon atom;

forming a resist upper layer film on the resist middle layer film by using a resist upper layer film composition comprising a photoresist composition, to form a multilayer resist film;

forming a resist pattern on the resist upper layer film by exposing a pattern circuit region of the resist upper layer film and then developing the same with a developer;

forming a resist middle layer film pattern by etching the resist middle layer film using the obtained resist pattern as an etching mask;

forming a resist under layer film pattern by etching the resist under layer film using the obtained resist middle layer film pattern as an etching mask; and further forming a pattern on the substrate to be processed by etching the substrate to be processed using the obtained resist under layer film pattern as an etching mask.

In such a multilayer resist process, the patterning process using the inventive organic film composition can form a fine pattern on the substrate to be processed with high precision.

In this case, the step of etching the resist under layer film using the obtained resist middle layer film as an etching mask is preferably performed by using an etching gas mainly comprising an oxygen gas or a hydrogen gas.

The resist middle layer film containing a silicon atom shows etching resistance to an oxygen gas or a hydrogen gas, so that etching of the resist under layer film by using the resist middle layer film as an etching mask can be carried out by using an etching gas mainly comprising an oxygen gas or a hydrogen gas.

The present invention also provides a patterning process which is a process for forming a pattern on a substrate to be processed, comprising at least the steps of:

forming a resist under layer film on the substrate to be processed by using the foregoing organic film composition;

forming an inorganic hard mask middle layer film selected from any one of a silicon oxide film, a silicon nitride film, and a silicon oxynitride film on the resist under layer film;

forming a resist upper layer film on the inorganic hard mask middle layer film by using a resist upper layer film composition comprising a photoresist composition, to form a multilayer resist film;

forming a resist pattern on the resist upper layer film by exposing a pattern circuit region of the resist upper layer film and then developing the same with a developer;

forming an inorganic hard mask middle layer film pattern by etching the inorganic hard mask middle layer film using the obtained resist pattern as an etching mask;

forming a resist under layer film pattern by etching the resist under layer film using the obtained inorganic hard mask middle layer film pattern as an etching mask; and further forming a pattern on the substrate to be processed by etching the substrate to be processed using the obtained resist under layer film pattern as an etching mask.

Further, the present invention provides a patterning process which is a process for forming a pattern on a substrate to be processed, comprising at least the steps of:

forming a resist under layer film on the substrate to be processed by using the foregoing organic film composition;

forming an inorganic hard mask middle layer film selected from any one of a silicon oxide film, a silicon nitride film, and a silicon oxynitride film on the resist under layer film;

forming an organic antireflection film on the inorganic hard mask middle layer film;

forming a resist upper layer film on the organic antireflection film by using a resist upper layer film composition comprising a photoresist composition, to form a multilayer resist film;

forming a resist pattern on the resist upper layer film by exposing a pattern circuit region of the resist upper layer film and then developing the same with a developer;

forming an inorganic hard mask middle layer film pattern by etching the organic antireflection film and the inorganic hard mask middle layer film using the obtained resist pattern as an etching mask;

forming a resist under layer film pattern by etching the resist under layer film using the obtained inorganic hard mask middle layer film pattern as an etching mask; and further forming a pattern on the substrate to be processed by etching the substrate to be processed using the obtained resist under layer film pattern as an etching mask.

Thus, a resist middle layer film may be formed on a resist under layer film, and an inorganic hard mask middle layer film selected from any one of a silicon oxide film, a silicon nitride film, and a silicon oxynitride film may be formed on the resist under layer film. Further, a photoresist film may be formed on the inorganic hard mask middle layer film as a resist upper layer film, and an organic antireflection film (BARC) is formed on the inorganic hard mask middle layer film by spin coating, and a photoresist film may be formed thereon. When a silicon oxynitride film (SiON film) is used as an inorganic hard mask middle layer film, it is possible to suppress reflection by virtue of the two-layer antireflective films, i.e., the SiON film and BARC film, even by a liquid immersion exposure at a higher NA exceeding 1.0. As another merit of forming the BARC, it is possible to mention an effect to reduce footing of a photoresist pattern just above the SiON film.

In the patterning process of the present invention, the inorganic hard mask middle layer film can be formed by a CVD method or an ALD method.

In the patterning process of the present invention, the inorganic hard mask middle layer film formed by the CVD method or the ALD method can be used in combination with the resist under layer film formed by the spin coating method.

It is preferable to use a substrate to be processed having a structure or step(s) each with a height of 30 nm or more as the substrate to be processed.

The inventive organic film composition is excellent in filling/planarizing characteristics, so that it is particularly useful for forming a pattern on a substrate to be processed having a structure or step(s) each with a height of 30 nm or more by a multilayer resist process lithography.

The present invention also provides a compound represented by the following general formula (1),

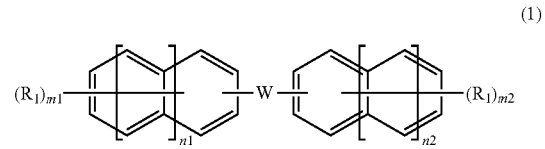

(1)

wherein n1 and n2 each independently represent 0 or 1; "W" represents a single bond or any of structures represented by the following formula (2); $R_1$ represents any of structures represented by the following general formula (3); m1 and m2 each independently represent an integer of 0 to 7, with the proviso that m1+m2 is 1 to 14;

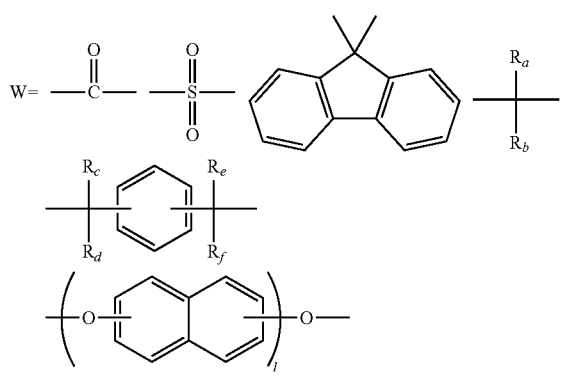

(2)

wherein "l" represents an integer of 0 to 3; $R_a$ to $R_f$ each independently represent a hydrogen atom, or an alkyl group having 1 to 10 carbon atoms, a phenyl group, or a phenylethyl group which may be substituted by a fluorine atom, and $R_a$ and $R_b$ may be bonded to each other to form a ring compound;

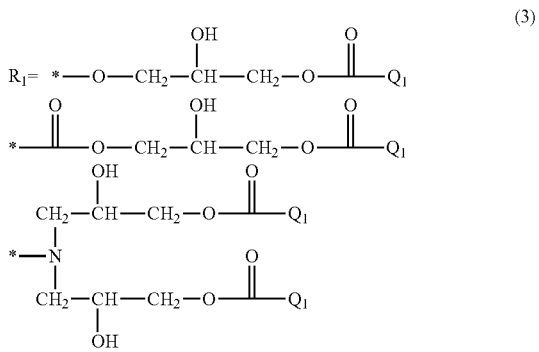

(3)

wherein "*" represents a bonding site to the aromatic ring; $Q_1$ represents a linear or branched saturated or unsaturated hydrocarbon group having 1 to 30 carbon atoms, an alicyclic group having 4 to 20 carbon atoms, or a substituted or unsubstituted phenyl group, naphthyl group, anthracenyl group, or pyrenyl group, and the methylene group constituting $Q_1$ may be substituted by an oxygen atom or a carbonyl group when $Q_1$ represents a linear or branched saturated or unsaturated hydrocarbon group having 1 to 30 carbon atoms.

When the inventive compound is used as a component of the organic film composition, the obtained organic film composition can form an organic film having both of high dry etching resistance and high filling/planarizing characteristics.

As described above, the present invention can provide a compound useful for the component of the organic film composition to form an organic film having both of high dry etching resistance and high filling/planarizing characteristics, and an organic film composition which contains this compound. Moreover, this organic film composition can be an organic film composition having excellent filling/planarizing characteristics without deteriorating the other properties such as heat resistance and etching resistance, and accordingly it is very useful for a resist under layer film composition in a multilayer resist process such as a two-layer resist process, a three-layer resist process using a silicon-containing middle layer film, and a four-layer resist process using a silicon-containing middle layer film and an organic antireflection film; or a planarizing film for manufacturing a semiconductor apparatus, for example.

Moreover, in the process for forming an organic film of the present invention, it is possible to form a sufficiently cured planarized organic film on a substrate to be processed.

Furthermore, by the patterning process of the present invention, it is possible to form a fine pattern on the substrate to be processed with high precision in a multilayer resist process.

DETAILED DESCRIPTION OF THE PREFERRED EMBODIMENTS

Figure 1:
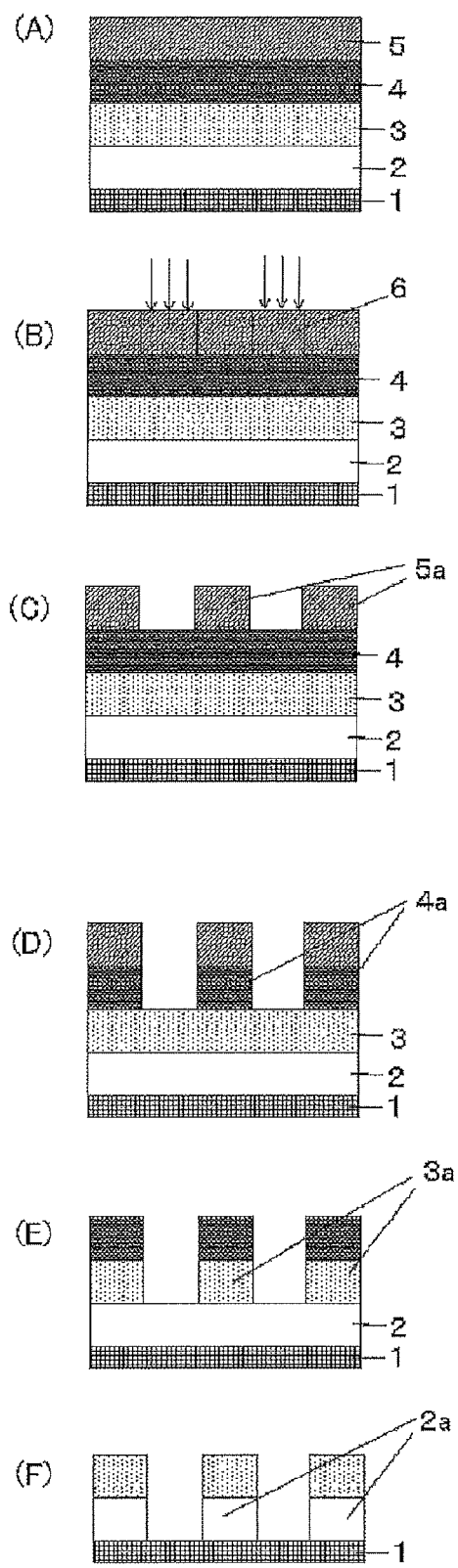
FIG. 1 is an explanatory view of an example of a patterning process using the three-layer resist process of present invention.

As described above, it has been sought an organic film composition for forming an organic film having both of dry etching resistance and advanced filling/planarizing characteristics.

The present inventors have diligently investigated to solve the problem described above, and have found that an organic film composition comprising a compound represented by the following general formula (1) can be an organic film composition which has both of high dry etching resistance and advanced filling/planarizing characteristics, and thus have completed the present invention.

That is to say, the present invention is an organic film composition comprising a compound represented by the following general formula (1),

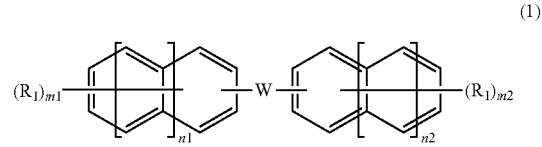

(1)

wherein n1 and n2 each independently represent 0 or 1; "W" represents a single bond or any of structures represented by the following formula (2); $R_1$ represents any of structures represented by the following general formula (3); m1 and m2 each independently represent an integer of 0 to 7, with the proviso that m1+m2 is 1 to 14;

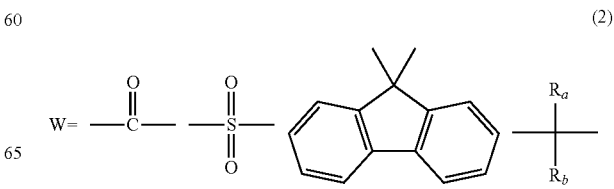

(2)

-continued

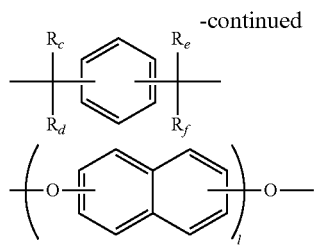

wherein "l" represents an integer of 0 to 3; $R_a$ to $R_f$ each independently represent a hydrogen atom, or an alkyl group having 1 to 10 carbon atoms, a phenyl group, or a phenylethyl group which may be substituted by a fluorine atom, and $R_a$ and $R_b$ may be bonded to each other to form a ring compound;

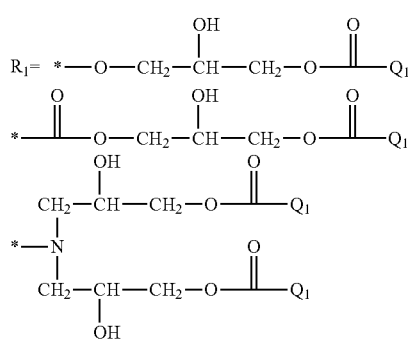

wherein "*" represents a bonding site to the aromatic ring; $Q_1$ represents a linear or branched saturated or unsaturated hydrocarbon group having 1 to 30 carbon atoms, an alicyclic group having 4 to 20 carbon atoms, or a substituted or unsubstituted phenyl group, naphthyl group, anthracenyl group, or pyrenyl group, and the methylene group constituting $Q_1$ may be substituted by an oxygen atom or a carbonyl group when $Q_1$ represents a linear or branched saturated or unsaturated hydrocarbon group having 1 to 30 carbon atoms.

In the following, the embodiment of the present invention will be explained in more detail, but the present invention is not limited thereto.

[Compound]

The inventive compound is a compound represented by the following general formula (1),

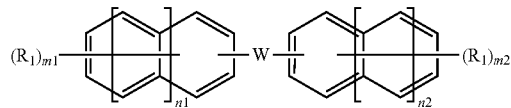

wherein n1 and n2 each independently represent 0 or 1; "W" represents a single bond or any of structures represented by the following formula (2); $R_1$ represents any of structures represented by the following general formula (3); m1 and m2 each independently represent an integer of 0 to 7, with the proviso that m1+m2 is 1 to 14;

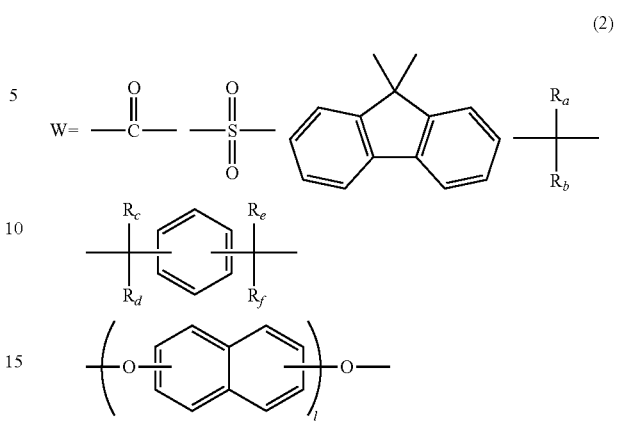

wherein "l" represents an integer of 0 to 3; $R_a$ to $R_f$ each independently represent a hydrogen atom, or an alkyl group having 1 to 10 carbon atoms, a phenyl group, or a phenylethyl group which may be substituted by a fluorine atom, and $R_a$ and $R_b$ may be bonded to each other to form a ring compound;

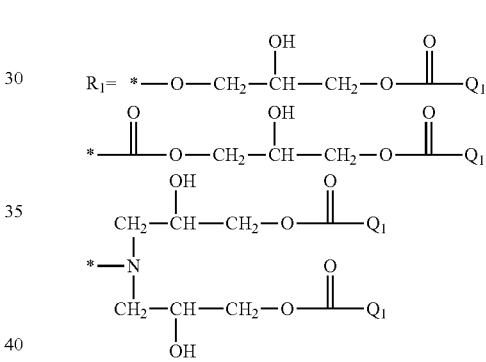

wherein "*" represents a bonding site to the aromatic ring; $Q_1$ represents a linear or branched saturated or unsaturated hydrocarbon group having 1 to 30 carbon atoms, an alicyclic group having 4 to 20 carbon atoms, or a substituted or unsubstituted phenyl group, naphthyl group, anthracenyl group, or pyrenyl group, and the methylene group constituting $Q_1$ may be substituted by an oxygen atom or a carbonyl group when $Q_1$ represents a linear or branched saturated or unsaturated hydrocarbon group having 1 to 30 carbon atoms.

As the compound represented by the foregoing general formula (1) which contains a linkage of a single bond or any of structures represented by the foregoing formula (2) as "W", the following structures can be preferably illustrated:

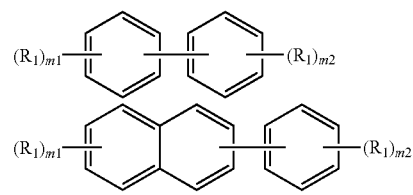

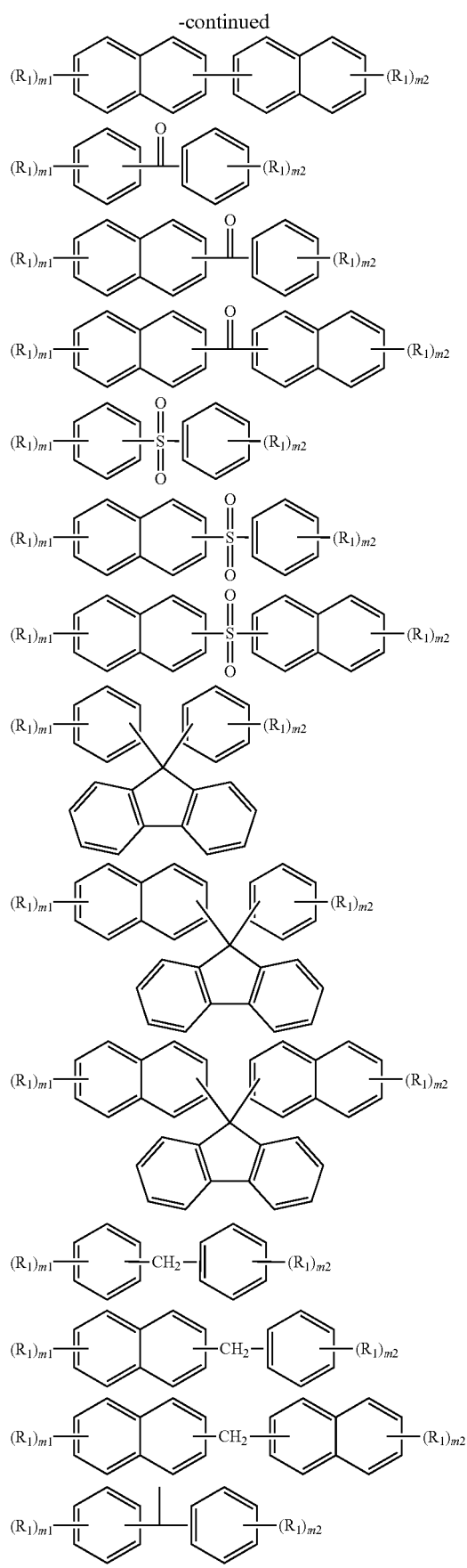
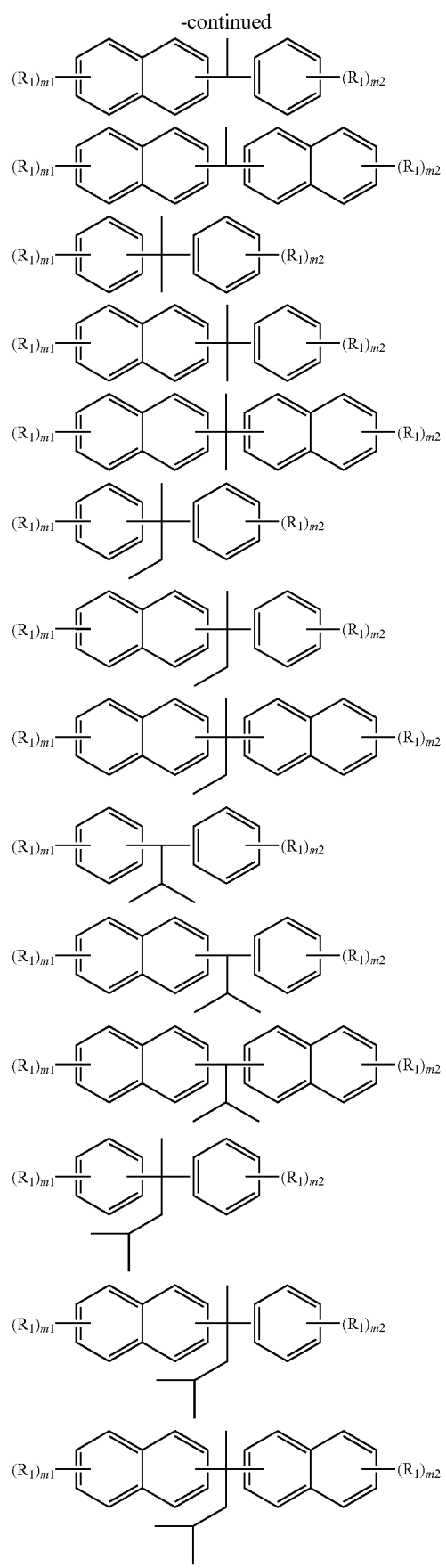

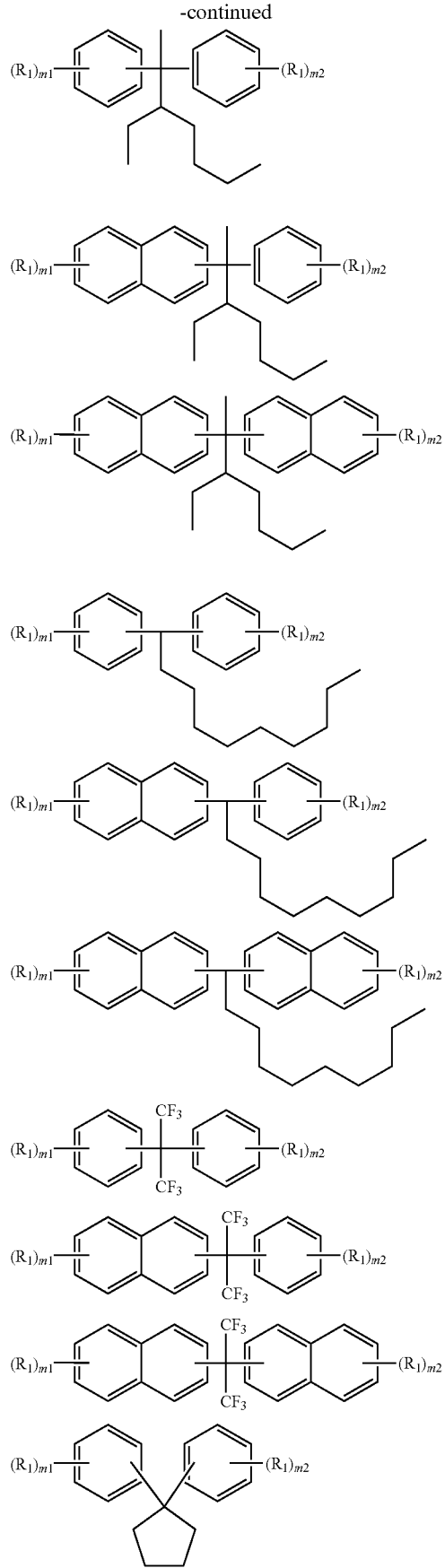
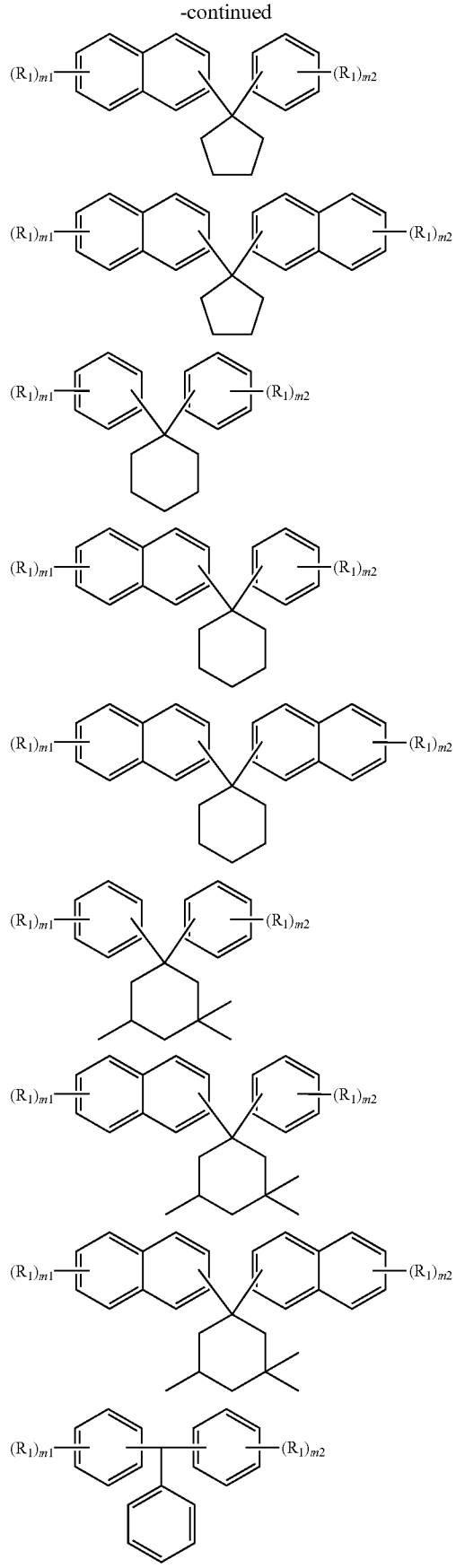

-continued
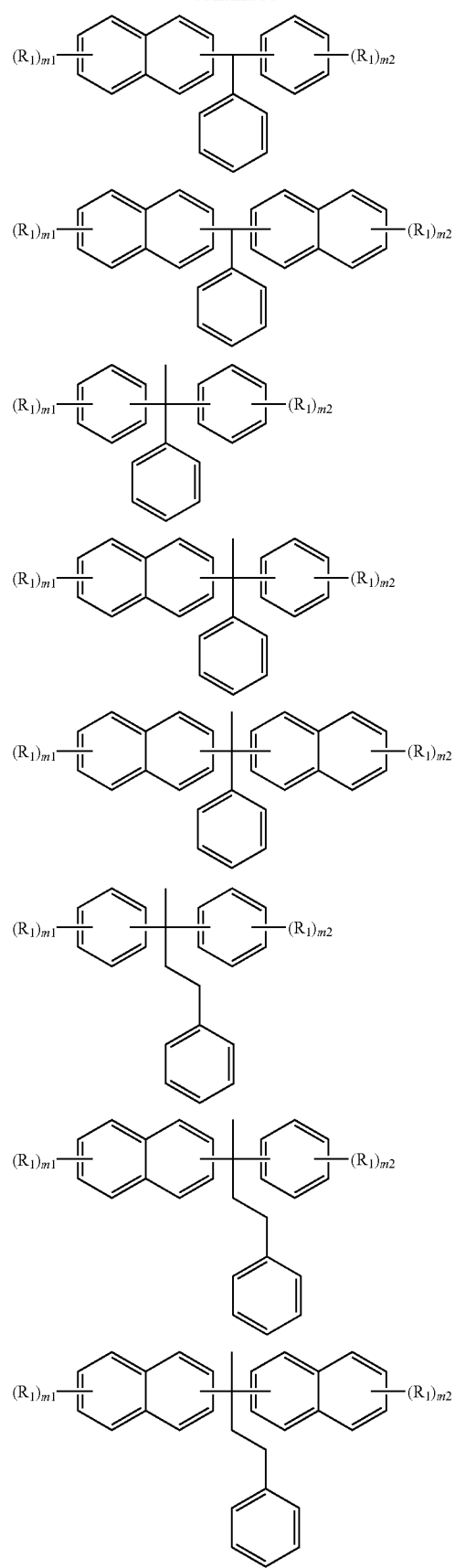
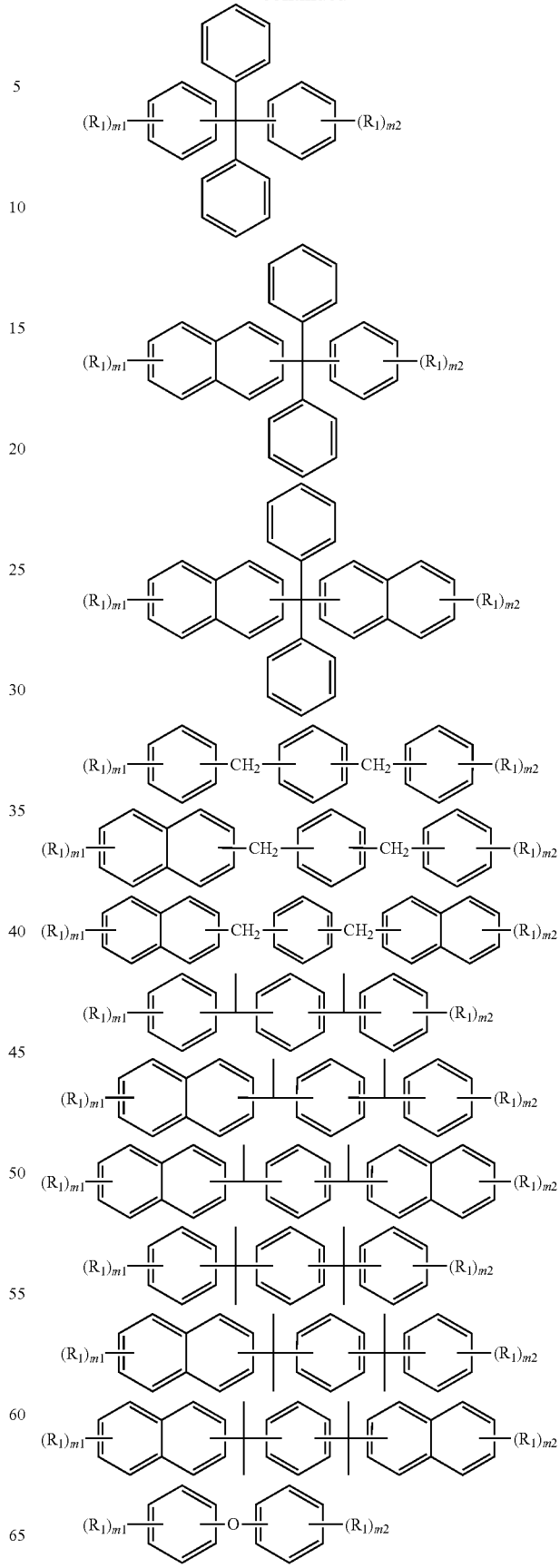

-continued

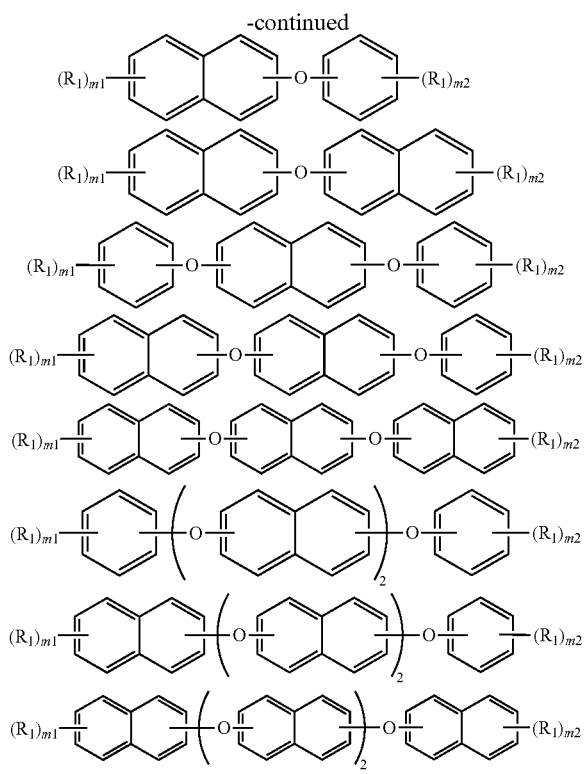

wherein, $R_1$, m1, and m2 have the same meanings as in the foregoing.

Among the general formula (1), the compound containing the naphthalene structure represented by the following general formula (4) is preferable so as to obtain dry etching resistance and heat resistance,

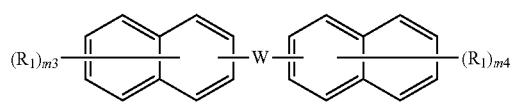

(4)

wherein, m3 and m4 represent 1 or 2, and "W" and $R_1$ have the same meanings as in the foregoing.

Furthermore, the coupling group "W" is preferably a single bond or any of structures represented by the following formula (5),

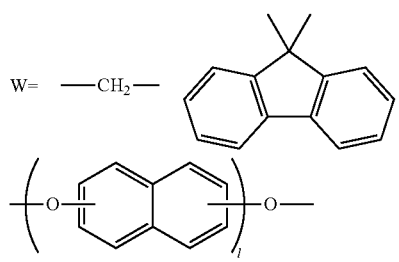

(5)

wherein, "l" has the same meaning as in the foregoing.

In the general formula (3), $Q_1$ represents a linear or branched saturated or unsaturated hydrocarbon group having 1 to 30 carbon atoms, an alicyclic group having 4 to 20 carbon atoms, or a substituted or unsubstituted phenyl group, naphthyl group, anthracenyl group, or pyrenyl group. When $Q_1$ represents a linear or branched saturated or unsaturated hydrocarbon group having 1 to 30 carbon atoms, the methylene group constituting $Q_1$ may be substituted by an oxygen atom or a carbonyl group.

Illustrative examples of the hydrocarbon group or the alicyclic group include a methyl group, an ethyl group, a n-propyl group, an isopropyl group, a n-butyl group, a sec-butyl group, a tert-butyl group, a n-pentyl group, a neopentyl group, a n-hexyl group, a n-heptyl group, a n-octyl group, a n-nonyl group, a n-decyl group, a n-dodecyl group, a n-pentadecyl group, a n-icosyl group, a cyclopentyl group, a cyclohexyl group, a cyclopentylmethyl group, a cyclohexylmethyl group, a cyclopentylethyl group, a cyclohexylethyl group, a cyclopentylbutyl group, a cyclohexyl butyl group, a norbornyl group, an adamantyl group, etc.

Furthermore, $Q_1$ may be a substituted or unsubstituted phenyl group, naphthyl group, anthracenyl group, or pyrenyl group. Illustrative examples of the substituent include a halogen atom, a hydrocarbon group, a hydroxyl group, an alkoxy group, a nitro group, a cyano group, etc.

Among these, a substituted or unsubstituted naphthyl group, anthracenyl group, or pyrenyl group is preferable in view of etching resistance and heat resistance.

Moreover, the compound represented by the general formula (1) preferably has two or more $Q_1$ in the molecule, and contains one or more structures represented by the following general formula (6) and one or more structures represented by the following general formula (7) respectively as $Q_1$,

 (6)

wherein "**" represents a bonding site to the carbonyl group; $R_h$ represents a linear or branched saturated or unsaturated hydrocarbon group having 1 to 30 carbon atoms, and the methylene group constituting $R_h$ may be substituted by an oxygen atom or a carbonyl group,

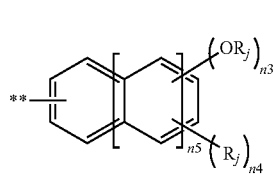 (7)

wherein "**" represents a bonding site to the carbonyl group; $R_i$ represents a hydrogen atom, or a linear or branched hydrocarbon group having 1 to 10 carbon atoms; $R_j$ represents a linear or branched hydrocarbon group having 1 to 10 carbon atoms, a halogen atom, a nitro group, an amino group, a nitrile group, an alkoxycarbonyl group having 1 to 10 carbon atoms, or an alkanoyloxy group having 1 to 10 carbon atoms; n3 and n4 represent the numbers of substituents on the aromatic ring, and each represent an integer of 0 to 7, with the proviso that n3+n4 is 0 to 7; n5 represents 0 to 2.

In the organic film composition which contains such a compound, it is possible to improve the filling/planarizing characteristics by enhancing thermal fluidity without deteriorating the heat resistance and etching resistance, and it is also possible to control the optical constants. Particularly, in an exposure in multilayer ArF lithography, the reflective light can be suppressed by giving appropriate optical constants, and excellent resolution is achieved thereby. Incidentally, as the optical constants of the organic film composition, a refractive index n in a range of 1.3 to 1.9 and an extinction coefficient k in a range of 0.1 to 0.7 are preferable in order to suppress the reflective light.

The compound represented by the general formula (1) has a structure in which aromatic rings are coupled by a single bond or any of structures represented by the formula (2), thereby having high carbon density. Accordingly, the organic film composition which contains these compounds exhibits high dry etching resistance and excellent heat resistance. The structure of the coupling group "W" can be selected appropriately from various coupling groups to fit the desired property as shown in the formula (2). Particularly, by introducing a structure represented by the formula (5) as "W", heat resistance/etching resistance can be obtained without deteriorating the filling/planarizing characteristics. Moreover, the terminal part $R_1$ contains a flexible structure having 3 carbon atoms, which gives filling/planarizing characteristics, and a terminal group(s) $Q_1$. In the terminal group $Q_1$, it is possible to introduce a flexible hydrocarbon structure, which attributes to improve the filling/planarizing characteristics, and a rigid aromatic ring structure, which contributes to the etching resistance and the heat resistance, in any ratio to fit the desired property. As described above, in the organic film composition using these compounds, the filling/planarizing characteristics and the heat resistance/etching resistance can be compatible in a higher level.

Moreover, by using an organic film composition which contains such a compound for a resist under layer film composition to be used for forming a multilayer resist film applied to fine processing in a manufacturing step of a semiconductor apparatus and so on, it is possible to provide a resist under layer film composition to form a resist under layer film having both of high dry etching resistance and high filling/planarizing characteristics, a process for forming a resist under layer film, and a patterning process. Furthermore, in the present invention, it is also possible to provide a planarizing composition for manufacturing a semiconductor apparatus with excellent filling/planarizing characteristics applicable to planarization in the manufacturing step of a semiconductor apparatus other than multilayer resist processes.

[Producing Method of Compound]

As a means for obtaining the compound used for the organic film composition according to the present invention, the illustrative method includes an addition reaction of an epoxy compound such as the one represented by the following general formula (8) and a carboxylic acid compound represented by ($Q_1$-COOH) (monocarboxylic acid). Incidentally, $Q_1$ has the same meaning as in the foregoing.

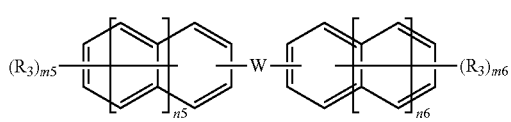

(8)

wherein, n5 and n6 each independently represent 0 or 1; $R_3$ represents any of structures represented by the following formula (9); m5 and m6 each independently represent an integer of 0 to 7, with the proviso that m5+m6 is 1 to 14; and "W" has the same meaning as in the foregoing,

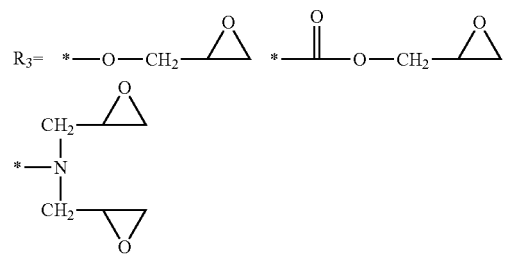

(9)

wherein "*" represents a bonding site to the aromatic ring.

In the reaction of the epoxy compound and the carboxylic acid compound, the loading amount of the carboxylic acid relative to 1 mole of the epoxy group in the epoxy compound is preferably 0.3 to 2.0 mole, more preferably 0.5 to 1.5 mole, further preferably 0.75 to 1.25 mole. When the loading amount of the carboxylic acid relative to the epoxy unit is appropriate as described above, it is possible to eliminate the risk due to the unreacted epoxy group being remained to deteriorate the storage stability of the organic film composition, and to prevent the unreacted carboxylic acid being remained to cause outgas.

Additionally, in the reaction of the epoxy compound and the carboxylic acid compound, it is possible to use plural carboxylic acid compounds represented by ($Q_1$-COOH) at the same time in the foregoing range of loading amount of the carboxylic acid in order to improve the required properties such as optical constants (n/k), thermal fluidity, etching resistance, heat resistance, and solubility to a solvent. As such a combination of the carboxylic acid compounds, it is particularly preferable to combine a carboxylic acid compound represented by the following general formula (10) (carboxylic acid compound (10)) and a carboxylic acid compound represented by the following general formula (11) (carboxylic acid compound (11)) at the same time. It is also possible to combine plural carboxylic acid compounds (10) and carboxylic acid compounds (11) at the same time. When the carboxylic acid compound(s) (10) and carboxylic acid compound(s) (11) are used at the same time, each loading amount can be adjusted in a range of 1 to 99% by mole based on the total loading amount of the carboxylic acid of 100% by mole. In view of the etching resistance and the heat resistance, preferably 20% by mole or more, more preferably 30% by mole or more of the carboxylic acid compound(s) (11) is used,

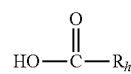

(10)

wherein, $R_h$ has the same meaning as in the foregoing,

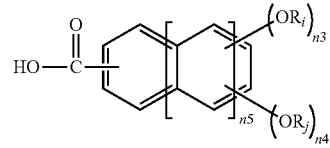

(11)

wherein, $R_i$, $R_j$, n3, n4, and n5 have the same meanings as in the foregoing.

The foregoing compound can be generally obtained by reacting an epoxy compound and a carboxylic acid compound in the presence of a reaction catalyst in a solvent-free condition or in a solvent at room temperature or with cooling or heating in case of need.

Illustrative examples of the solvent include alcohols such as methanol, ethanol, isopropyl alcohol, butanol, ethylene glycol, propylene glycol, diethylene glycol, glycerol, methyl cellosolve, ethyl cellosolve, butyl cellosolve, and propylene glycol monomethyl ether; ethers such as diethyl ether, dibutyl ether, diethylene glycol diethyl ether, diethylene glycol dimethyl ether, tetrahydrofuran, and 1,4-dioxane; chlorinated solvents such as methylene chloride, chloroform, dichloroethane, and trichloroethylene; hydrocarbons such as hexane, heptane, benzene, toluene, xylene, and cumene, nitriles such as acetonitrile; ketones such as acetone, ethyl methyl ketone, and isobutyl methyl ketone; esters such as ethyl acetate, n-butyl acetate, and propylene glycol methyl ether acetate; lactones such as γ-butyrolactone; aprotic polar solvents such as dimethyl sulfoxide, N,N-dimethylformamide, and hexamethyl phosphoric triamide. These can be used singly or as a mixture of two or more kinds. These solvents may be used in a range of 0 to 2,000 parts by mass relative to 100 parts by mass of the reaction raw materials.

Illustrative examples of the reaction catalyst include quaternary ammonium salts such as benzyltriethylammonium chloride, benzyltriethylammonium bromide, benzyltrimethylammonium chloride, tetramethylammonium chloride, tetramethylammonium bromide, tetramethylammonium iodide, tetramethylammonium hydroxide, tetraethylammonium bromide, tetrabutylammonium chloride, tetrabutylammonium bromide, tetrabutylammonium iodide, tetrabutylammonium hydrogen sulfate, trioctylmethylammonium chloride, tributylbenzylammonium chloride, trimethylbenzylammonium chloride, trimethylbenzylammonium hydroxide, N-laurylpyridinium chloride, N-lauryl-4-picolinium chloride, N-laurylpicolinium chloride, trimethylphenylammonium bromide, and N-benzylpicolinium chloride; quaternary phosphonium salts such as tetrabutylphosphonium chloride, tetrabutylphosphonium bromide, and tetraphenylphosphonium chloride; and tertiary amines such as tris[2-(2-methoxyethoxy)ethyl]amine, tris(3,6-dioxaheptyl)amine, tris(3,6-dioxaoctyl)amine. The amount of the catalyst is preferably 0.001 to 100% by mass, more preferably 0.005 to 50% by mass based on the raw material. The reaction temperature is preferably −50° C. to the boiling point of a solvent, more preferably room temperature to 150° C. The reaction time can be appropriately selected from 0.1 to 100 hours.

Illustrative examples of the reaction method include a method of loading an epoxy compound, a carboxylic acid compound, and a catalyst collectively; a method of dispersing or dissolving an epoxy compound and a carboxylic acid compound followed by adding a catalyst collectively or dropping a catalyst diluted by a solvent; or a method of dispersing or dissolving a catalyst followed by adding an epoxy compound and a carboxylic acid compound collectively or dropping an epoxy compound and a carboxylic acid compound diluted with a solvent. The reactant can be directly used as an organic film composition after a completion of the reaction, or may be subjected to dilution with an organic solvent, liquid separation and washing, and then recovered in order to eliminate the unreacted raw materials, a catalyst, and so on remaining in the system.

The organic solvent used in this case is not particularly limited if it can dissolve the compound and separate into two phases when mixed with water. Illustrative examples thereof include hydrocarbons such as hexane, heptane, benzene, toluene, and xylene; esters such as ethyl acetate, n-butyl acetate, and propylene glycol methyl ether acetate; ketones such as methyl ethyl ketone, methyl amyl ketone, cyclohexanone, and methyl isobutyl ketone; ethers such as diethyl ether, diisopropyl ether, methyl tert-butyl ether, and ethyl cyclopentylmethyl ether; chlorinated solvents such as methylene chloride, chloroform, dichloroethane, and trichloroethylene; and mixtures thereof. As the washing water used in this case, the one generally called deionized water or ultra pure water may be used. The washing may be performed one time or more, preferably about 1 to 5 times since 10 times or more of washing does not always exert full effects thereof.

In liquid separation and washing, the washing may be performed with aqueous basic solution in order to eliminate the unreacted carboxylic acid or an acidic component in the system. Illustrative examples of the base include hydroxides of alkaline metal, carbonates of alkaline metal, hydroxides of alkaline earth metal, carbonates of alkaline earth metal, ammonia, and organic ammonium salts.

Furthermore, in liquid separation and washing, the washing may be performed with aqueous acidic solution in order to eliminate the metal impurity or a basic component in the system. Illustrative examples of the acid include inorganic acids such as hydrochloric acid, hydrobromic acid, sulfuric acid, nitric acid, phosphoric acid, and heteropolyacid; organic acids such as oxalic acid, trifluoroacetic acid, methanesulfonic acid, benzenesulfonic acid, p-toluenesulfonic acid, and trifluoromethanesulfonic acid.

The foregoing washing may be performed with either the aqueous basic solution or the aqueous acidic solution, or may be performed by combining both of them. The liquid separation and washing is preferably carried out in the order with aqueous basic solution and subsequently with aqueous acidic solution in view of eliminating a metal impurity.

After the foregoing washing with aqueous basic solution and/or aqueous acidic solution, washing with neutral water may be performed subsequently. The washing may be carried out one time or more, preferably about 1 to 5 times. As the neutral water, deionized water or ultra pure water described above may be used. The washing may be carried out one time or more, however, fewer washings cannot always eliminate a basic component or acidic component. Preferably, washing is carried out for about 1 to 5 times since 10 times or more of washing does not always exert full effects thereof.

The reaction product after the separating operation can be recovered as a powder by crystallizing operation or by condensing and drying the solvent under reduced pressure or atmospheric pressure. It is also possible to maintain it in a solution state with an appropriate concentration in order to improve the workability when preparing the organic film composition. In this case, the concentration is preferably 0.1 to 50% by mass, more preferably 0.5 to 30% by mass. Such a concentration helps to prevent deteriorating the workability since its viscosity does not become too high, and becomes also economical since the amount of solvent does not become too much.

The organic solvent used in this case is not particularly limited if it can dissolve the compound. Illustrative examples thereof include ketones such as cyclohexanone and methyl 2-amyl ketone; alcohols such as 3-methoxybutanol, 3-methyl-3-methoxybutanol, 1-methoxy-2-propanol, 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate. These can be used singly or as a mixture of two or more kinds.

In the preparation of these compounds, a carboxylic acid compound can be incorporated in accordance with a required property. It is possible to combine a flexible hydrocarbon structure, which contributes to improve the filling/planarizing characteristics, and a rigid aromatic ring structure, which contributes to the etching resistance and the heat resistance, in any ratio. In the organic film composition using these compounds, the filling/planarizing characteristics and the heat resistance/etching resistance can be compatible in a higher level.

To the compound of the present invention, a substituent of a condensed aromatic group or an alicyclic group can be introduced. Illustrative examples of the substituent which can be introduced herein include the following.

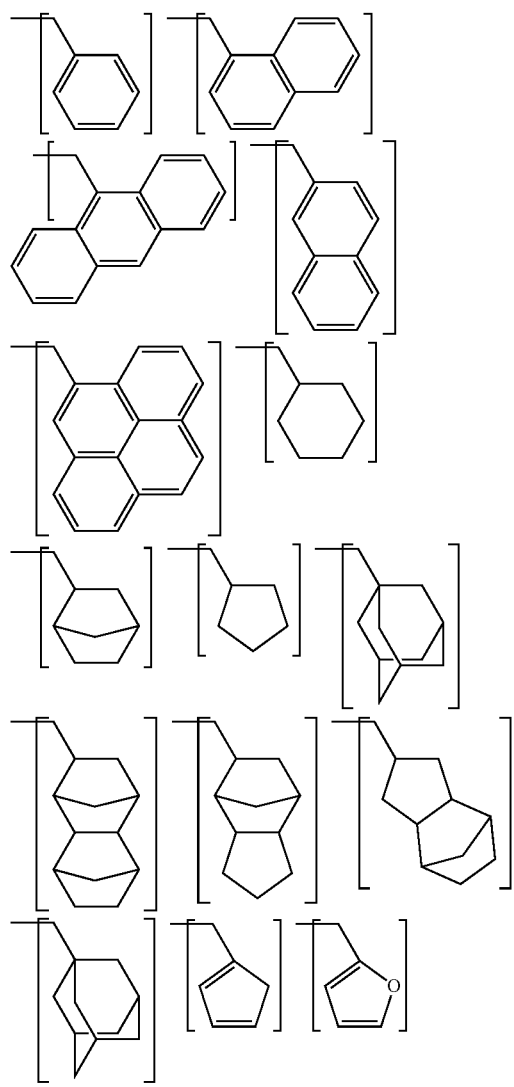

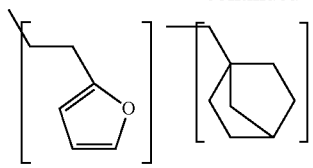

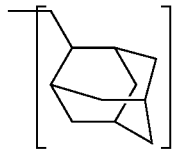

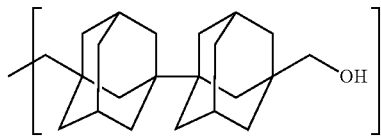

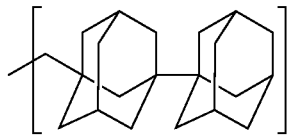

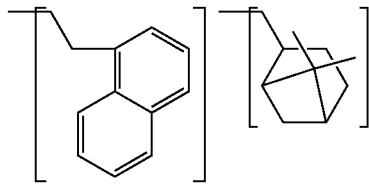

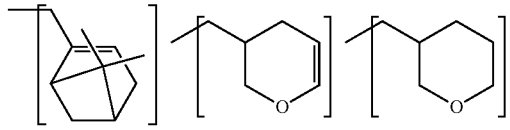

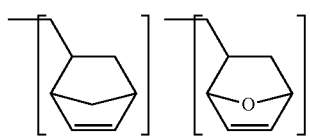

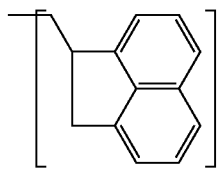

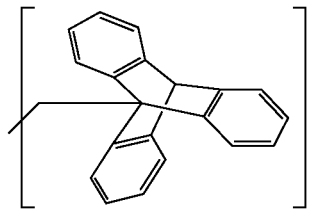

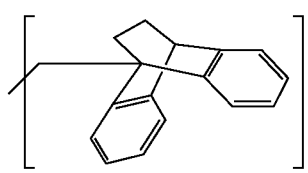

-continued

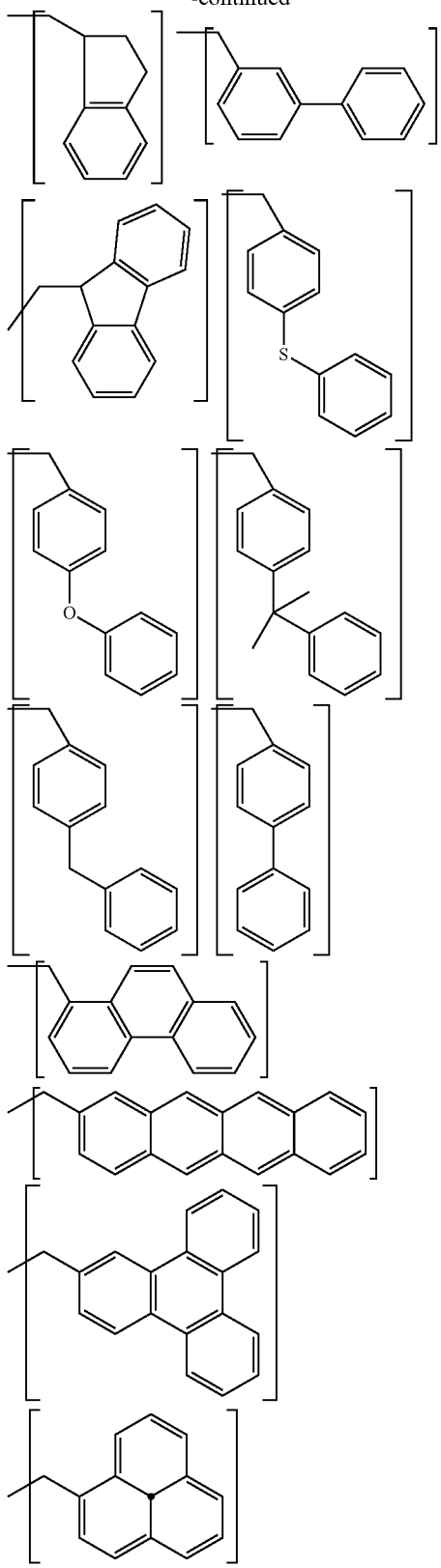

Among these, polycyclic aromatic groups such as an anthracenemethyl group and a pyrenemethyl group can be used most preferably for exposure to a wavelength of 248 nm. In order to improve the transparency at 193 nm, a group with an alicyclic structure or a naphthalene structure is preferably used. On the other hand, a benzene ring has a window to enhance the transparency at a wavelength of 157 nm, and accordingly it is preferable to shift the absorption wavelength to enhance the absorption. With a furan ring, the absorption wavelength get shorter than a benzene ring and the absorption at 157 nm is enhanced slightly, although the effect is small. A naphthalene ring, an anthracene ring, or a pyrene ring makes an absorption wavelength longer to enhance the absorption. These aromatic rings also have an effect to improve the etching resistance, and are preferably used.

As a method to introduce the substituent, a method through a reaction mechanism of aromatic electrophilic substitution is mentioned, the method comprises introducing an alcohol with the hydroxyl group being at the position of the bonding site of the substituent into the ortho position or para position to the hydroxyl group, the alkyloxy group, or the alkyl group under an acid catalyst. Illustrative examples of the acid catalyst include acidic catalysts such as hydrochloric acid, nitric acid, sulfuric acid, formic acid, oxalic acid, acetic acid, methanesulfonic acid, n-butanesulfonic acid, camphorsulfone acid, tosic acid, and trifluoromethanesulfonic acid. The amount of the acid catalyst is preferably 0.001 to 20 parts by mass based on 100 parts by mass of the compounds before the reaction. The introducing amount of the substituent is in a range of 0 to 0.8 mole based on 1 mole of the compound.

<Organic Film Composition>

An organic film composition of the present invention is a composition comprising a compound represented by the following general formula (1),

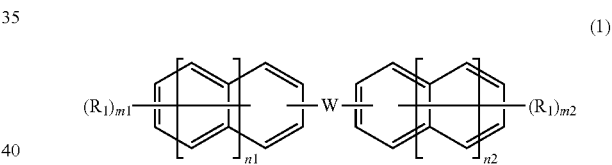

(1)

wherein n1 and n2 each independently represent 0 or 1; "W" represents a single bond or any of structures represented by the following formula (2); $R_1$ represents any of structures represented by the following general formula (3); m1 and m2 each independently represent an integer of 0 to 7, with the proviso that m1+m2 is 1 to 14;

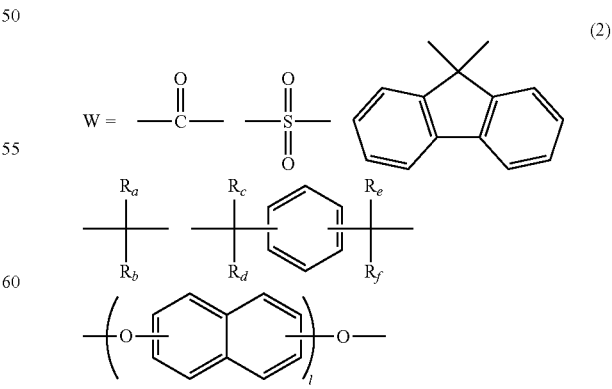

(2)

wherein "l" represents an integer of 0 to 3; $R_a$ to $R_f$ each independently represent a hydrogen atom, or an alkyl group having 1 to 10 carbon atoms, a phenyl group, or a phenylethyl group which may be substituted by a fluorine atom, and $R_a$ and $R_b$ may be bonded to each other to form a ring compound;

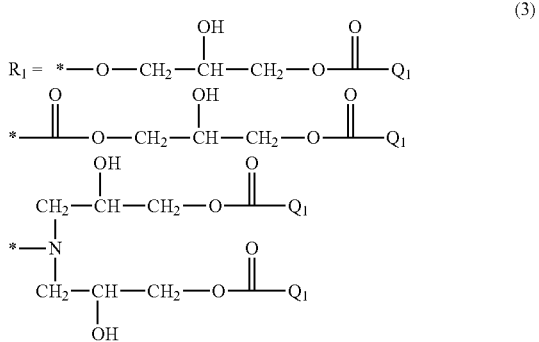

wherein "*" represents a bonding site to the aromatic ring; $Q_1$ represents a linear or branched saturated or unsaturated hydrocarbon group having 1 to 30 carbon atoms, an alicyclic group having 4 to 20 carbon atoms, or a substituted or unsubstituted phenyl group, naphthyl group, anthracenyl group, or pyrenyl group, and the methylene group constituting $Q_1$ may be substituted by an oxygen atom or a carbonyl group when $Q_1$ represents a linear or branched saturated or unsaturated hydrocarbon group having 1 to 30 carbon atoms.

The inventive organic film composition can be blended another polymer. The compound for blending or the polymer for blending is blended with the inventive organic film composition to play a role to improve the film formability in spin coating or filling property on the substrate having a step. For such a compound or a polymer, material with high carbon atom density and high etching resistance is selected. Illustrative examples thereof include novolac resins of phenol, o-cresol, m-cresol, p-cresol, 2,3-dimethylphenol, 2,5-dimethylphenol, 3,4-dimethylphenol, 3,5-dimethylphenol, 2,4-dimethylphenol, 2,6-dimethylphenol, 2,3,5-trimethylphenol, 3,4,5-trimethylphenol, 2-tert-butylphenol, 3-tert-butylphenol, 4-tert-butylphenol, 2-phenylphenol, 3-phenylphenol, 4-phenylphenol, 3,5-diphenylphenol, 2-naphthylphenol, 3-naphthylphenol, 4-naphthylphenol, 4-tritylphenol, resorcinol, 2-methylresorcinol, 4-methylresorcinol, 5-methylresorcinol, catechol, 4-tert-butylcatechol, 2-methoxyphenol, 3-methoxyphenol, 2-propylphenol, 3-propylphenol, 4-propylphenol, 2-isopropylphenol, 3-isopropylphenol, 4-isopropylphenol, 2-methoxy-5-methylphenol, 2-tert-butyl-5-methylphenol, pyrogallol, thymol, isothymol, 4,4'-(9H-fluorene-9-ylidene)bisphenol, 2,2'-dimethyl-4,4'-(9H-fluorene-9-ylidene)bisphenol, 2,2'-diallyl-4,4'-(9H-fluorene-9-ylidene)bisphenol, 2,2'-difluoro-4,4'-(9H-fluorene-9-ylidene)bisphenol, 2,2'-diphenyl-4,4'-(9H-fluorene-9-ylidene)bisphenol, 2,2'-dimethoxy-4,4'-(9H-fluorene-9-ylidene)bisphenol, 2,3,2',3'-tetrahydro-(1,1')-spirobiindene-6,6'-diol, 3,3,3',3'-tetramethyl-2,3,2',3'-tetrahydro-(1,1')-spirobiindene-6,6'-diol, 3,3,3',3',4,4'-hexamethyl-2,3,2',3'-tetrahydro-(1,1')-spirobiindene-6,6'-diol, 2,3,2',3'-tetrahydro-(1,1')-spirobiindene-5,5'-diol, 5,5'-dimethyl-3,3,3',3'-tetramethyl-2,3,2',3'-tetrahydro-(1,1')-spirobiindene-6,6'-diol, 1-naphthol, 2-naphthol, 2-methyl-1-naphthol, 4-methoxy-1-naphthol, 7-methoxy-2-naphthol, dihydroxynaphthalenes such as 1,5-dihydroxynaphthalene, 1,7-dihydroxynaphthalene, and 2,6-dihydroxynaphthalene, methyl 3-hydroxynaphthalene-2-carboxylate, indene, hydroxyindene, benzofuran, hydroxyanthracene, acenaphthylene, biphenyl, bisphenol, trisphenol, dicyclopentadiene, tetrahydroindene, 4-vinylcyclohexene, norbornadiene, 5-vinylnorborna-2-ene, α-pinene, β-pinene, and limonene, etc.; polyhydroxystyrene, polystyrene, polyvinylnaphthalene, polyvinylanthracene, polyvinylcarbazole, polyindene, polyacenaphthylene, polynorbornene, polycyclodecene, polytetracyclododecene, polynortricyclene, poly(meth)acrylate, and copolymers thereof. It is also possible to blend naphtholdicyclopentadiene copolymer described in JP 2004-205685A, fluorenebisphenolnovolac resin described in JP 2005-128509A, acenaphthylene copolymer described in JP 2005-250434A, fullerene having a phenol group described in JP 2006-227391A, a bisphenol compound and novolac resin thereof described in JP 2006-293298A, novolac resin of an adamantanephenol compound described in JP 2006-285095A, a bisnaphthol compound and novolac resin thereof described in JP 2010-122656A, a fullerene resin compound described in JP 2008-158002A. The blending amount of the compound for blending or the polymer for blending is preferably 0 to 1,000 parts by mass, more preferably 0 to 500 parts by mass based on 100 parts by mass of the organic film composition of the present invention.

Into the organic film composition of the present invention, (A) an acid generator and (B) a cross-linking agent can be added to further accelerate a thermal cross-linking reaction. As (A) the acid generators, it is possible to add any of the one which generates an acid by thermal decomposition and the one which generates an acid by light irradiation. Specifically, compositions described in paragraphs (0061) to (0085) of JP 2007-199653A can be added.

As (B) the cross-linking agent usable for the organic film composition of the present invention, materials described in paragraphs (0055) to (0060) of JP 2007-199653A can be added.

Further, into the organic film composition of the present invention, (C) a surfactant can be added to improve coating property in spin coating. As the surfactant (C), it is possible to use those described in paragraphs (0142) to (0147) of JP 2009-269953A.

As (D) the organic solvent usable in the organic film composition of the present invention, those which can dissolve (A) an acid generator, (B) a cross-linking agent, and (C) a surfactant are preferred. Specifically, the solvents described in paragraphs (0091) to (0092) of JP 2007-199653A can be added. Of these, propylene glycol monomethyl ether acetate, propylene glycol monomethyl ether, 2-heptanone, cyclopentanone, cyclohexanone, γ-butyrolactone, and a mixture of two or more kinds of these solvents are preferably used.

Furthermore, into the organic film composition of the present invention, a basic compound can be blended to improve the storage stability. The basic compound acts as a quencher to an acid to inhibit a cross-linking reaction by trace amount of the acid generated from the acid generator. Specifically, materials described in paragraphs (0086) to (0090) of JP 2007-199653A can be added as such a basic compound.

Also, into the organic film composition of the present invention, an additive to further improve filling/planarizing characteristics may be added in addition to the foregoing components.

The additive is not particularly limited so long as it provides filling/planarizing characteristics, and preferably used are, for example, a liquid state additive having a polyethylene glycol or polypropylene glycol structure, or a thermo-decomposable polymer having a weight loss ratio between 30° C. and 250° C. of 40% by mass or more and a weight average molecular weight of 300 to 200,000. The thermo-decomposable polymer preferably contains a repeating unit having an acetal structure represented by the following general formula (DP1) or (DP1a):

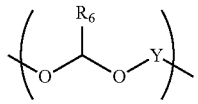
(DP1)

wherein $R_6$ represents a hydrogen atom or a saturated or unsaturated monovalent organic group having 1 to 30 carbon atoms which may be substituted; and "Y" represents a saturated or unsaturated divalent organic group having 2 to 30 carbon atoms;

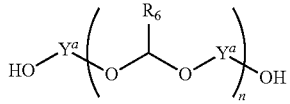
(DP1a)

wherein $R_{6a}$ represents an alkyl group having 1 to 4 carbon atoms; $Y^a$ represents a saturated or unsaturated divalent hydrocarbon group having 4 to 10 carbon atoms, which may have an ether bond; and "n" represents an average repeating unit number and is 3 to 500.

Incidentally, the inventive organic film composition can be used singly or as a mixture of two or more kinds. The organic film composition can be used for a resist under layer film composition or a planarizing composition for manufacturing a semiconductor apparatus.

The inventive organic film composition is also very useful for a resist under layer film composition in a multilayer resist process such as a two-layer resist process, a three-layer resist process using a silicon-containing middle layer film, and a four-layer resist process using a silicon-containing inorganic hard mask middle layer film and an organic antireflection film.

(Process for Forming an Organic Film)

The present invention provides a process for forming an organic film which acts as a resist under layer film of a multilayer resist film used in lithography or a planarizing film for manufacturing a semiconductor apparatus by using the foregoing organic film composition.

In the process for forming an organic film of the present invention, a substrate to be processed is coated with the organic film composition by a method such as a spin coating method. Using a spin coating method and so on, an excellent filling property can be obtained. After spin coating, the solvent is evaporated, and then baking (heat treatment) thereof is carried out to accelerate the cross-linking reaction in order to prevent mixing of the composition with a resist upper layer film or a resist middle layer film. The baking is preferably carried out at a temperature in the range of 100° C. or higher and 600° C. or lower for 10 to 600 seconds, more preferably at a temperature in the range of 200° C. or higher and 500° C. or lower for 10 to 300 seconds. In consideration of an influence on device damage and wafer deformation, the upper limit of the heating temperature in a wafer process of lithography is preferably 600° C. or lower, more preferably 500° C. or lower.

Further, in the process for forming an organic film of the present invention, it is also possible to form an organic film by coating a substrate to be processed with the inventive organic film composition by a spin coating method and so on as described above, and baking the organic film composition under an atmosphere with an oxygen concentration of 0.1% or more and 21% or less, thereby curing the organic film composition.

The inventive organic film composition is baked in such an oxygen atmosphere, thereby enabling to obtain a sufficiently cured film.

Baking atmosphere may be air, and inert gas such as $N_2$, Ar and He may be filled. Also, a baking temperature, etc., may be employed as mentioned above.

Such an inventive process for forming an organic film can provide a flat cured film irrespective of unevenness of the substrate to be processed due to its excellent filling/planarizing characteristics, so that it is extremely useful for forming a flat cured film on a substrate to be processed having a structure or step(s) with a height of 30 nm or more.

Incidentally, a thickness of the organic film such as the resist under layer film or the planarizing film for manufacturing a semiconductor apparatus can be optionally selected, and is preferably 30 to 20,000 nm, particularly preferably 50 to 15,000 nm.

(Patterning Process)

As a patterning process by a three-layer resist process using such an organic film composition, the present invention provides a patterning process which is a process for forming a pattern on a substrate to be processed, comprising at least the steps of: forming a resist under layer film on the substrate to be processed by using the organic film composition of the present invention; forming a resist middle layer film (silicon-containing resist middle layer film) on the resist under layer film by using a resist middle layer film composition containing a silicon atom; forming a resist upper layer film on the resist middle layer film by using a resist upper layer film composition comprising a photoresist composition, to form a multilayer resist film; forming a resist pattern on the resist upper layer film by exposing a pattern circuit region of the resist upper layer film and then developing the same with a developer; forming a resist middle layer film pattern by etching the resist middle layer film using the obtained resist pattern as an etching mask; forming a resist under layer film pattern by etching the resist under layer film using the obtained resist middle layer film pattern as an etching mask; and further forming a pattern on the substrate to be processed by etching the substrate to be processed using the obtained resist under layer film pattern as an etching mask.

The silicon-containing resist middle layer film of the three-layer resist process shows etching resistance to an oxygen gas or a hydrogen gas, so that in the three-layer resist process, it is preferred to carry out the etching of the resist under layer film using the resist middle layer film as a mask under an etching gas mainly comprising an oxygen gas or a hydrogen gas.

As the silicon-containing resist middle layer film in the three-layer resist process, a polysilsesquioxane-based middle layer film is also preferably used. This makes the resist middle layer film possess an antireflective effect, thereby enabling to restrict reflection. Particularly, when a material configured to contain many aromatic groups so as to possess a higher substrate-etching resistance is used as a resist under layer film for 193 nm exposure, a k value is rather increased to increase a substrate reflection. Nonetheless, the reflection is restricted by the resist middle layer film, thereby enabling to restrict the substrate reflection down to 0.5% or less. Preferably used as the resist middle layer film having an antireflective effect is a polysilsesquioxane, which has a pendant anthracene for exposure of 248 nm or 157 nm, or a pendant phenyl group or a pendant light-absorbing group having a silicon-silicon bond for 193 nm exposure, and which is cross-linked by an acid or a heat.

In this case, formation of a silicon-containing resist middle layer film by the spin coating method is easy and convenient than that by the CVD method so that it has a merit in a cost.

Further, an inorganic hard mask middle layer film may be formed as a middle layer film. In this case, the process comprises at least the steps of: forming a resist under layer film on the substrate to be processed by using the organic film composition of the present invention; forming an inorganic hard mask middle layer film selected from any one of a silicon oxide film, a silicon nitride film, and a silicon oxynitride film on the resist under layer film; forming a resist upper layer film on the inorganic hard mask middle layer film by using a resist upper layer film composition comprising a photoresist composition; forming a resist pattern on the resist upper layer film by exposing a pattern circuit region of the resist upper layer film and then developing the same with a developer; forming an inorganic hard mask middle layer film pattern by etching the inorganic hard mask middle layer film using the obtained resist pattern as an etching mask; forming a resist under layer film pattern by etching the resist under layer film using the obtained inorganic hard mask middle layer film pattern as an etching mask; and further forming a pattern on the substrate to be processed by etching the substrate to be processed using the obtained resist under layer film pattern as an etching mask.

As mentioned above, when the inorganic hard mask middle layer film is formed on the resist under layer film, a silicon oxide film, a silicon nitride film, and a silicon oxynitride film (SiON film) can be formed by the CVD method or the ALD method. The method for forming a silicon nitride film is described in, for example, JP 2002-334869A and WO2004/066377. A film thickness of the inorganic hard mask middle layer film is preferably 5 to 200 nm, more preferably 10 to 100 nm. As the inorganic hard mask middle layer film, a SiON film which has high effects as an antireflection film is most preferably used. A temperature of the substrate in forming the SiON film is raised up to 300° C. to 500° C., so that it is necessary to endure the temperature of 300° C. to 500° C. as the under layer. The organic film composition to be used in the present invention has high heat resistance, and endures the high temperature of 300° C. to 500° C., so that the inorganic hard mask middle layer film formed by the CVD method or the ALD method, and the resist under layer film formed by the spin coating method can be used in combination.

Further, the present invention can be suitably used for a four-layer resist process using an organic antireflection film. In this case, the process comprises at least the steps of: forming a resist under layer film on the substrate to be processed by using the organic film composition of the present invention; forming an inorganic hard mask middle layer film selected from any one of a silicon oxide film, a silicon nitride film, and a silicon oxynitride film on the resist under layer film; forming an organic antireflection film on the inorganic hard mask middle layer film; forming a resist upper layer film on the organic antireflection film by using a resist upper layer film composition comprising a photoresist composition, to form a multilayer resist film; forming a resist pattern on the resist upper layer film by exposing a pattern circuit region of the resist upper layer film and then developing the same with a developer; forming an inorganic hard mask middle layer film pattern by etching the organic antireflection film and the inorganic hard mask middle layer film using the obtained resist pattern as an etching mask; forming a resist under layer film pattern by etching the resist under layer film using the obtained inorganic hard mask middle layer film pattern as an etching mask; and further forming a pattern on the substrate to be processed by etching the substrate to be processed using the obtained resist under layer film pattern as an etching mask.

Although it may form a photoresist film on the inorganic hard mask middle layer film as a resist upper layer film as mentioned above, it is also possible to form an organic antireflection film (BARC) on the inorganic hard mask middle layer film by spin coating, and a photoresist film may be formed thereon. In particular, when a SiON film is used as the inorganic hard mask middle layer film, it is possible to suppress reflection by virtue of the two-layer antireflective films of the SiON film and the BARC film, even by a liquid immersion exposure at a higher NA exceeding 1.0. As another merit of forming the BARC, it is possible to mention an effect to reduce footing of a photoresist pattern just above the SiON film.

The resist upper layer film in the three-layer resist process may be a positive type or a negative type, and it is possible to use therefor the same one as a typically used photoresist composition. Prebaking is carried out after spin coating of the photoresist composition, preferably at 60 to 180° C. for 10 to 300 seconds. Thereafter, exposure is carried out according to a usual manner, followed by post-exposure baking (PEB) and development, to thereby obtain a resist pattern. Although a thickness of the resist upper layer film is not particularly limited, it is preferably 30 to 500 nm, particularly preferably 50 to 400 nm.

Further, examples of light for exposure include high energy beams at wavelengths of 300 nm or shorter, specifically excimer lasers at 248 nm, 193 nm, and 157 nm, soft X-rays at 3 to 20 nm, an electron beam, X-rays, and the like.

Next, etching is carried out by using the obtained resist pattern as a mask. In a three-layer resist process, etching of a resist middle layer film or an inorganic hard mask middle layer film is carried out by using the resist pattern as a mask and by the use of a fluorocarbon-based gas. The resist middle layer film pattern or the inorganic hard mask middle layer film pattern can be formed thereby.

Then, etching processing of the resist under layer film is carried out by using the obtained resist middle layer film pattern or inorganic hard mask middle layer film pattern as a mask.

The subsequent etching of a substrate to be processed can be also carried out by a usual method: for example, performing etching mainly using a fluorocarbon-based gas when the substrate to be processed is made of $SiO_2$, SiN or silica-based low dielectric constant insulating film; or etching mainly using a chlorine-based or bromine-based gas for a substrate made of p-Si, Al or W. When substrate processing is carried out by etching with a fluorocarbon-based gas, the silicon-containing middle layer film pattern of the three-layer process is stripped simultaneously with the substrate processing. When the etching is carried out by using a chlorine-based gas or a bromine-based gas, dry etching stripping by using a fluorocarbon-based gas have to be separately carried out after the substrate processing to strip the silicon-containing middle layer film pattern.

The resist under layer film obtained from the inventive organic film composition has a characteristic of exhibiting excellent etching resistance in the etching of these substrates to be processed.

It is noted that the substrate to be processed is not particularly limited, and a substrate made of Si, α-Si, p-Si, $SiO_2$, SiN, SiON, W, TiN or Al, or a substrate in which a layer to be processed is formed thereon may be used. Examples of the layer to be processed include various Low-k films made of Si, $SiO_2$, SiON, SiN, p-Si, α-Si, W, W—Si, Al, Cu or Al—Si, and stopper films thereof, which can each typically form into a thickness of 50 to 10,000 nm, particularly 100 to 5,000 nm. When the layer to be processed is formed, different material is used for each of the substrate and the layer to be processed.

It is preferable to use a substrate to be processed having a structure or step(s) each with a height of 30 nm or more as the substrate to be processed.

An example of the three-layer resist process will be specifically explained by referring to FIG. 1 as follows.

In the case of the three-layer resist process, as shown in FIG. 1(A), the process is configured to form a resist under layer film 3 by using the inventive organic film composition on a layer to be processed 2 laminated on a substrate 1, to thereafter form a resist middle layer film 4 thereon, and to form a resist upper layer film 5 thereon.

Next, as shown in FIG. 1(B), exposure is carried out for required portions 6 of the resist upper layer film, followed by PEB and development, to form a resist pattern 5a (FIG. 1(C)). The obtained resist pattern 5a is then used as a mask, etching of the resist middle layer film 4 is carried out by using a CF-based gas to form a resist middle layer film pattern 4a (FIG. 1(D)). After removing the resist pattern 5a, the obtained resist middle layer film pattern 4a is used as a mask, etching of the resist under layer film 3 is carried out by using an oxygen plasma to form a resist under layer film pattern 3a (FIG. 1(E)). Further, after removing the resist middle layer film pattern 4a, the resist under layer film pattern 3a is used as a mask, etching of the layer to be processed 2 is carried out to form a pattern 2a (FIG. 1(F)).

When an inorganic hard mask middle layer film is used, the resist middle layer film 4 is the inorganic hard mask middle layer film, and when a BARC is to be arranged, a BARC layer is provided between the resist middle layer film 4 and the resist upper layer film 5. Etching of the BARC may be continuously carried out prior to etching of the resist middle layer film 4, or etching of the BARC alone may be performed and subsequently etching of the resist middle layer film 4 may be carried out by changing an etching apparatus.

As described above, the patterning process of the present invention can form a fine pattern on the substrate to be processed with high precision in a multilayer resist process.

EXAMPLES

In the following, the present invention is explained in more detail by referring to Synthesis Examples, Comparative Synthesis Examples, Examples and Comparative Examples, but the present invention is not limited thereto.

Incidentally, the measurement of the molecular weight was carried out specifically by the following method. A weight average molecular weight (Mw) and a number average molecular weight (Mn) were measured by gel permeation chromatography (GPC) using tetrahydrofuran as an eluent, in terms of polystyrene, and the degree of dispersion (Mw/Mn) was calculated.

For the syntheses of compounds for the organic film composition, the following epoxy compounds (E-1) to (E-9) were used,

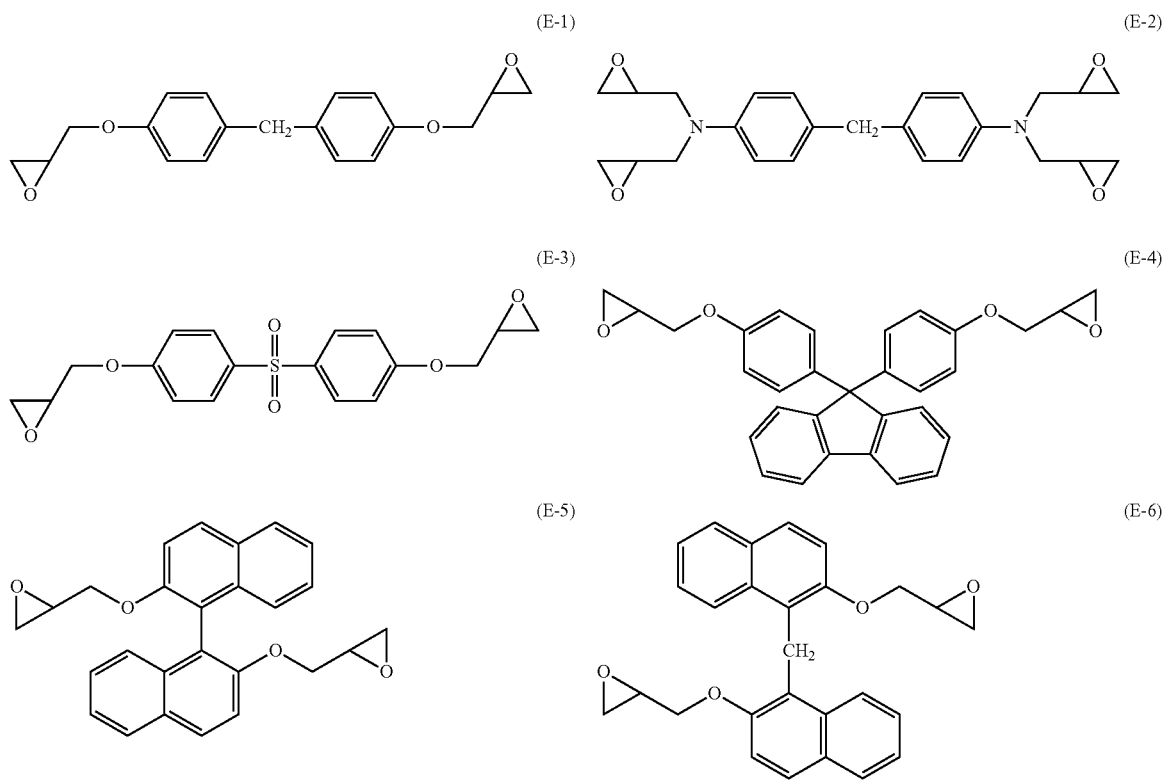

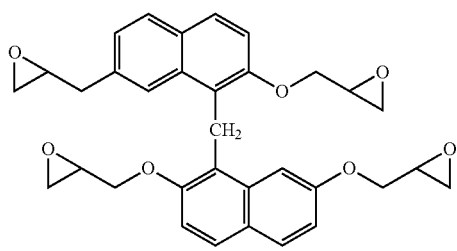
(E-7)

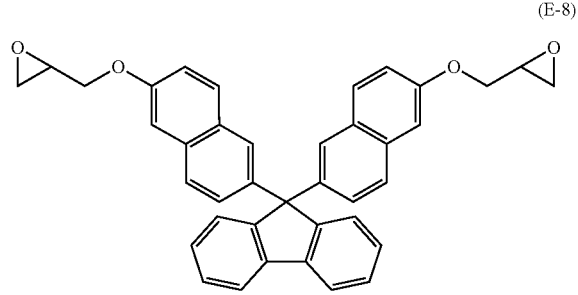
(E-8)

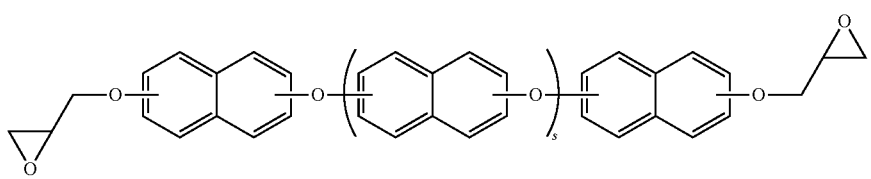
(E-9)

wherein, "s" represents an integer of 0 to 3.

(E-1) EXA-830LVP (product of DIC Corporation): epoxy equivalent: 160
(E-2) 4,4'-methylene-bis(N,N-diglycidylaniline): epoxy equivalent: 106
(E-3) EXA-1514 (product of DIC Corporation): epoxy equivalent: 300
(E-4) PG-100 (product of Osaka Gas Chemicals Co., Ltd.): epoxy equivalent: 260
(E-5) 2,2'-diglycidyloxy-1,1'-binaphthalene: epoxy equivalent: 232
(E-6) HP-4770 (product of DIC Corporation): epoxy equivalent: 204
(E-7) HP-4700 (product of DIC Corporation): epoxy equivalent: 162
(E-8) CG-500 (product of Osaka Gas Chemicals Co., Ltd.): epoxy equivalent: 310
(E-9) HP-6000 (product of DIC Corporation): epoxy equivalent: 245

For the syntheses of compounds for the organic film composition, the following carboxyl acid compounds (C-1) to (C-8) were used,

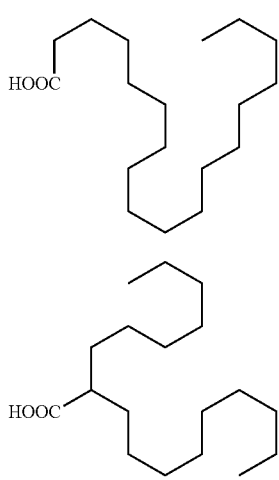

(C-1)

(C-2)

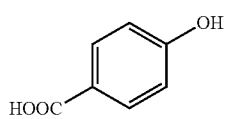
(C-3)

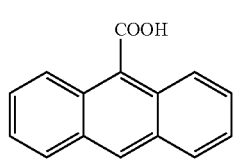
(C-4)

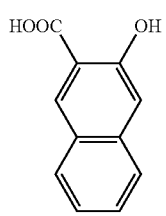
(C-5)

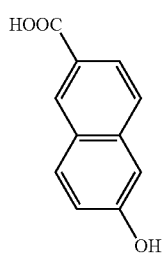
(C-6)

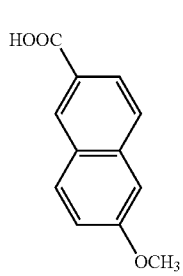
(C-7)

-continued

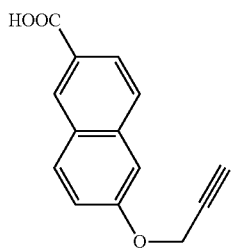

(C-8)

(C-1) stearic acid
(C-2) isostearic acid
(C-3) 4-hydroxybenzoic acid
(C-4) 9-anthracenecarboxylic acid
(C-5) 3-hydroxy-2-naphthoic acid
(C-6) 6-hydroxy-2-naphthoic acid
(C-7) 6-methoxy-2-naphthoic acid
(C-8) 6-propargyloxy-2-naphthoic acid

[Synthesis Example 1] Synthesis of Compound (A-1)

weight average molecular weights (Mw) and the degrees of dispersion (Mw/Mn) of these compounds were measured and shown in Tables 2 to 4.

TABLE 1

| Synthesis Example | Epoxy compound (1) | Carboxylic acid compound (1) | Carboxylic acid compound (2) | Carboxylic acid compound (3) |
|---|---|---|---|---|
| 1 | (E-1) 80.0 g | (C-5) 94.1 g | — | — |
| 2 | (E-2) 53.0 g | (C-4) 55.6 g | (C-6) 47.0 g | — |
| 3 | (E-3) 75 g | (C-7) 50.6 g | — | — |
| 4 | (E-4) 58.0 g | (C-3) 17.3 g | (C-6) 23.5 g | — |
| 5 | (E-4) 58.0 g | (C-5) 47.0 g | — | — |
| 6 | (E-5) 65.0 g | (C-6) 23.5 g | (C-7) 25.3 g | — |
| 7 | (E-6) 51.0 g | (C-5) 47.0 g | — | — |
| 8 | (E-6) 51.0 g | (C-8) 56.6 g | — | — |

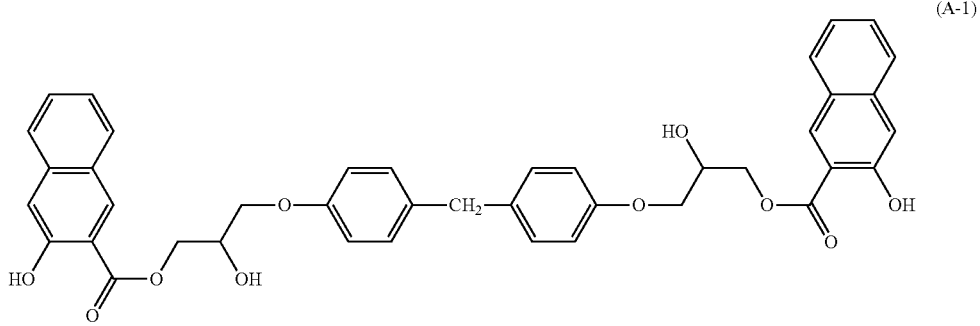 [SMILES: O=C(OCC(O)COc1ccc(Cc2ccc(OCC(O)COC(=O)c3cc4ccccc4cc3O)cc2)cc1)c1cc2ccccc2cc1O]

(A-1)

Under a nitrogen atmosphere, 80.0 g of Epoxy compound (E-1), 94.1 g of Carboxylic acid compound (C-5), and 600 g of 2-methoxy-1-propanol were mixed to homogeneous solution at a temperature of 100° C. Then, 5.7 g of benzyltriethylammonium chloride was added and stirred at a temperature of 120° C. for 12 hours. After being cooled to room temperature, 1,500 g of methyl isobutyl ketone was added, and the organic layer was washed with 300 g of pure water for 5 times. The organic layer was dried under reduced pressure to give Compound (A-1).

The weight average molecular weight (Mw) and the degree of dispersion (Mw/Mn) were measured by GPC to give following results:

(A-1): Mw=750, Mw/Mn=1.05

[Synthesis Examples 2 to 19] Syntheses of Compounds (A-2) to (A-19)

Compounds (A-2) to (A-19) shown in Tables 2 to 4 were obtained as products in the same condition as in Synthesis Example 1 except that the epoxy compounds and the carboxylic acid compounds shown in Table 1 were used. The TABLE 1-continued

| Synthesis Example | Epoxy compound (1) | Carboxylic acid compound (1) | Carboxylic acid compound (2) | Carboxylic acid compound (3) |
|---|---|---|---|---|
| 9 | (E-6) 51.0 g | (C-1) 17.8 g | (C-6) 35.3 g | — |
| 10 | (E-6) 51.0 g | (C-2) 14.2 g | (C-5) 37.6 g | — |
| 11 | (E-7) 40.5 g | (C-6) 47.0 g | — | — |
| 12 | (E-7) 40.5 g | (C-1) 17.8 g | (C-5) 35.3 g | — |
| 13 | (E-7) 40.5 g | (C-1) 7.1 g | (C-2) 7.1 g | (C-7) 40.4 g |
| 14 | (E-7) 40.5 g | (C-1) 17.8 g | (C-3) 8.6 g | (C-7) 25.3 g |
| 15 | (E-8) 77.5 g | (C-4) 27.8 g | (C-6) 23.5 g | — |
| 16 | (E-8) 77.5 g | (C-5) 47.0 g | — | — |
| 17 | (E-9) 61.3 g | (C-3) 34.5 g | — | — |
| 18 | (E-9) 61.3 g | (C-6) 47.0 g | — | — |
| 19 | (E-9) 61.3 g | (C-2) 17.8 g | (C-5) 35.3 g | — |

TABLE 2
| Synthesis Example | Compound | Mw | Mw/Mn |
|---|---|---|---|
| 1 | 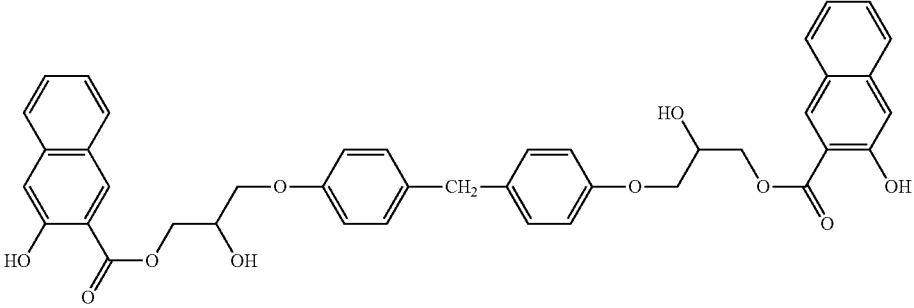 [SMILES: O=C(OCC(O)COc1ccc(Cc2ccc(OCC(O)COC(=O)c3cc4ccccc4cc3O)cc2)cc1)c1cc2ccccc2cc1O] (A-1) | 760 | 1.05 |
| 2 | 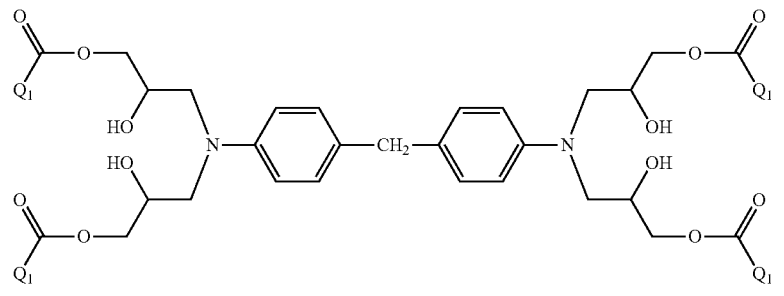 (A-2) 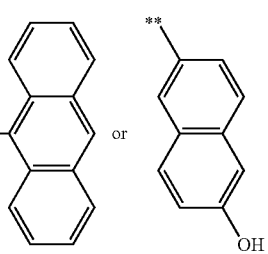 50:50 | 1350 | 1.18 |
| 3 | 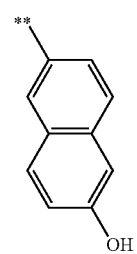 (A-3) | 780 | 1.03 |

TABLE 2-continued
| Synthesis Example | Compound | Mw | Mw/Mn |
|---|---|---|---|
| 4 | 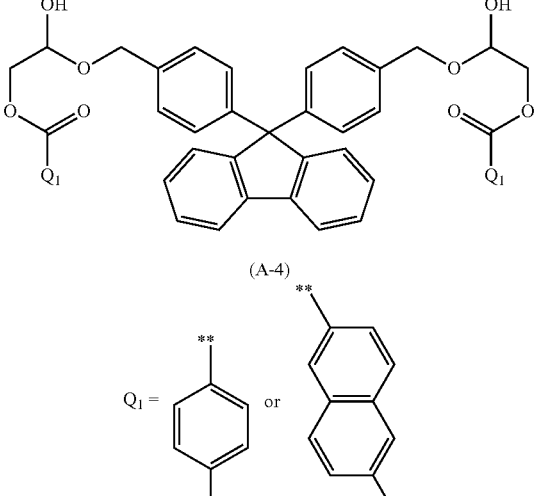 (A-4) 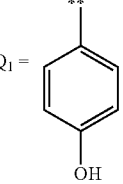 50:50 | 820 | 1.15 |
| 5 | 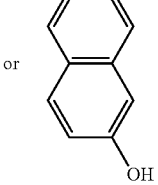 (A-5) | 910 | 1.08 |
| 6 | 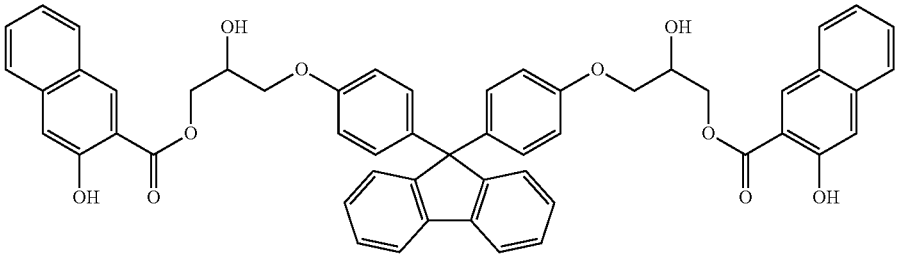 [SMILES: O=C(OCC(O)COc1ccc(C2(c3ccc(OCC(O)COC(=O)c4cc5ccccc5cc4O)cc3)c3ccccc3-c3ccccc32)cc1)c1cc2ccccc2cc1O] (A-6) 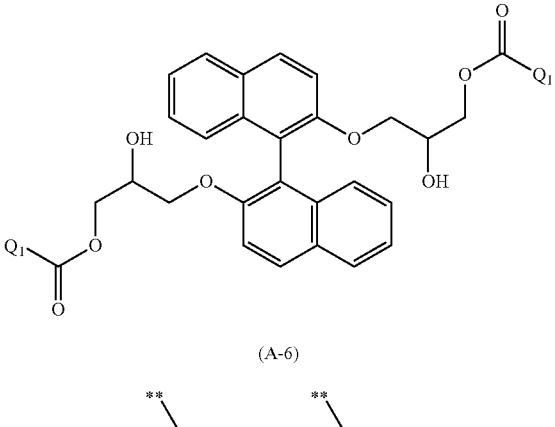 50:50 | 840 | 1.17 |

TABLE 3

| Synthesis Example | Compound | Mw | Mw/Mn |
|---|---|---|---|
| 7 | (A-7) | 870 | 1.05 |
| 8 | (A-8) | 900 | 1.04 |
| 9 | (A-9) | 950 | 1.24 |

$Q_1$ =  (alkyl chain) or  -naphthyl-OH

25:75

TABLE 3-continued
| Synthesis Example | Compound | Mw | Mw/Mn |
|---|---|---|---|
| 10 | 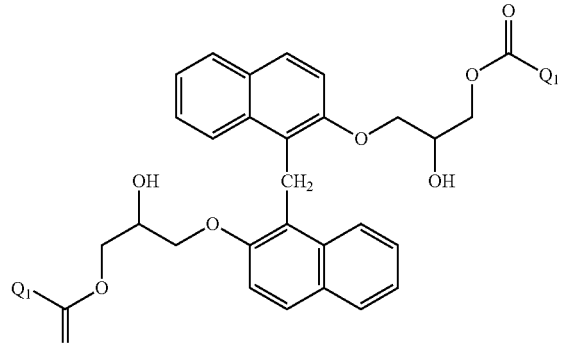 (A-10) 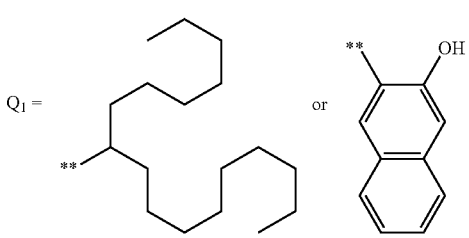 20:80 | 920 | 1.19 |
| 11 | 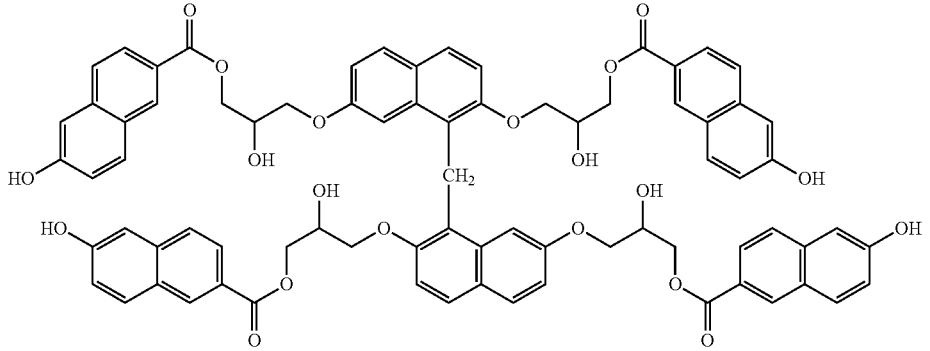 (A-11) | 1780 | 1.14 |
| 12 | 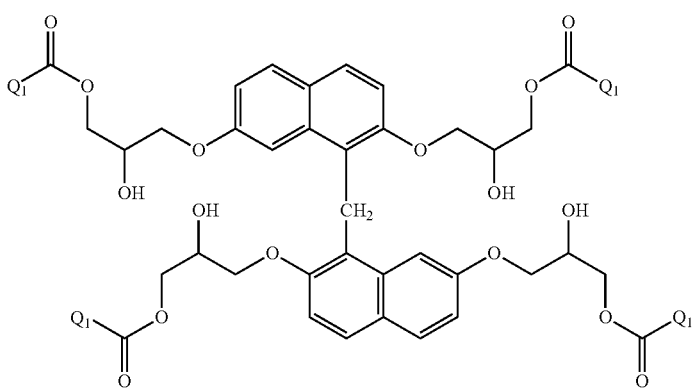 (A-12) | 1890 | 1.38 |

TABLE 3-continued
| Synthesis Example | Compound | Mw | Mw/Mn |
|---|---|---|---|
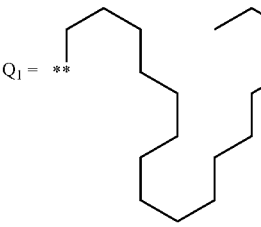
25:75
TABLE 4
| Synthesis Example | Compound | Mw | Mw/Mn |
|---|---|---|---|
| 13 | 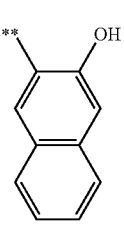 (A-13) | 1720 | 1.34 |
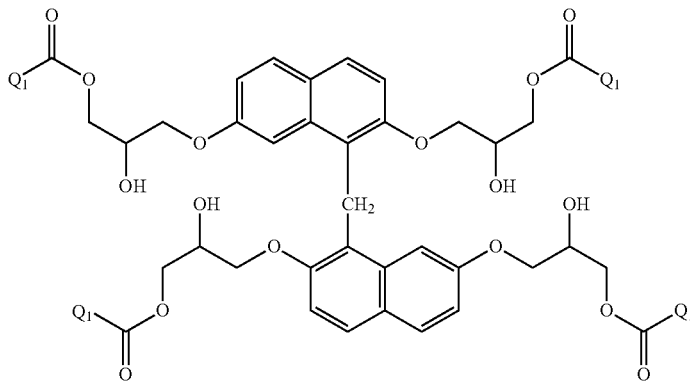
10:10:80
| | | | |
|---|---|---|---|
| 14 | 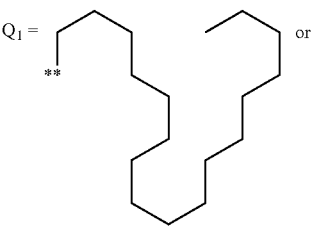 (A-14) | 1570 | 1.40 |

TABLE 4-continued
| Synthesis Example | Compound | Mw | Mw/Mn |
|---|---|---|---|
| 15 | 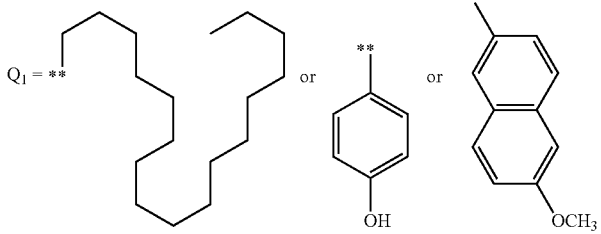 (A-15) | 990 | 1.13 |
| 16 | 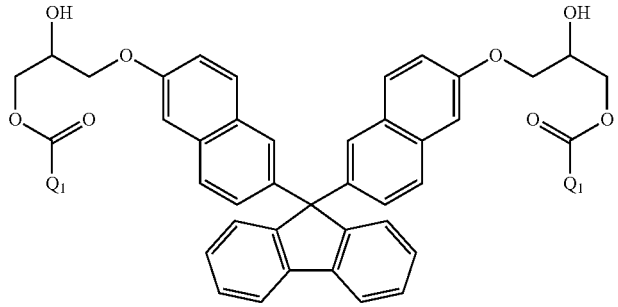  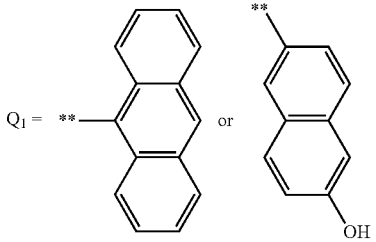 (A-16) | 960 | 1.03 |
| 17 | 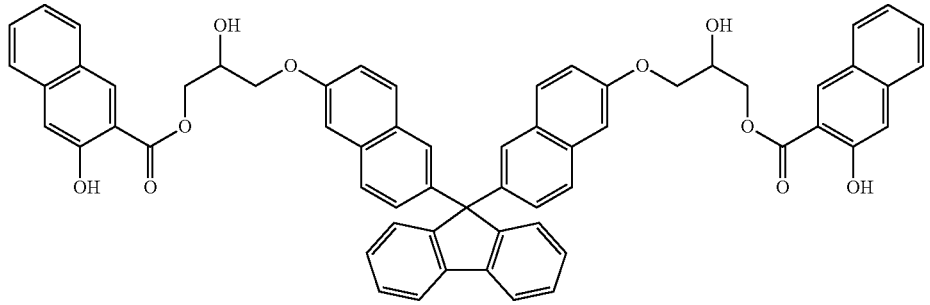 [SMILES: O=C(OCC(O)COc1ccc2cc(C3(c4ccc5cc(OCC(O)COC(=O)c6cc7ccccc7cc6O)ccc5c4)c4ccccc4-c4ccccc43)ccc2c1)c1cc2ccccc2cc1O] (A-17) | 850 | 1.05 |

TABLE 4-continued

| Synthesis Example | Compound | Mw | Mw/Mn |
|---|---|---|---|
| 18 | 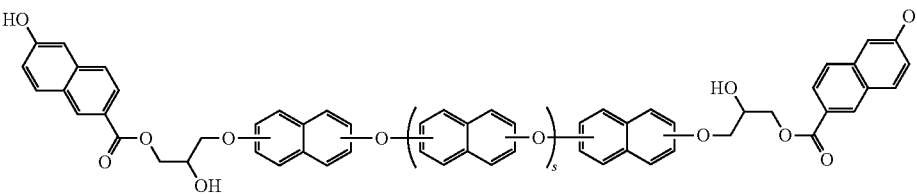 (A-18) | 920 | 1.05 |
| 19 | 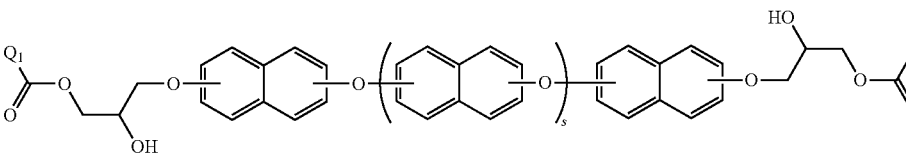 (A-19) | 1110 | 1.20 |
| | 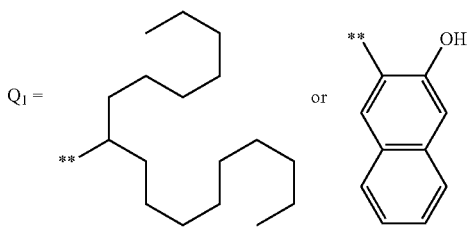 25:75 | | |

In Tables 2 to 4, the ratios in the structural formulae (A-2, A-4, A-6, A-9, A-10, A-12 to A-15, A-19) represent ratios of terminal group $Q_1$ in the compounds. "**" represents a bonding site to the carbonyl group. "s" has the same meaning as in the foregoing.

[Comparative Synthesis Example 1] Synthesis of Compound (R-1)

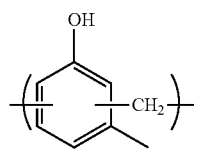

(R-1)

Under a nitrogen atmosphere, 54.1 g of m-cresol, 32.5 g of 37% formalin solution, and 250 g of 2-methoxy-1-propanol were mixed to homogeneous solution at a temperature of 80° C. Then, 18 g of 20% 2-methoxy-1-propanol solution of para-toluenesulfonic acid were slowly added and stirred at a temperature of 110° C. for 12 hours. After being cooled to room temperature, 500 g of methyl isobutyl ketone was added, and the organic layer was washed with 200 g of pure water for 5 times followed by drying the organic layer under reduced pressure. To the residue, 300 ml of THF was added, and a polymer was re-precipitated from 2,000 ml of hexane. The precipitated polymer was separated by filtration and dried under reduced pressure to give Compound (R-1).

The weight average molecular weight (Mw) and the degree of dispersion (Mw/Mn) were measured by GPC to give following results:
(R-1): Mw=6900, Mw/Mn=5.53

[Comparative Synthesis Example 2] Synthesis of Compound (R-2)

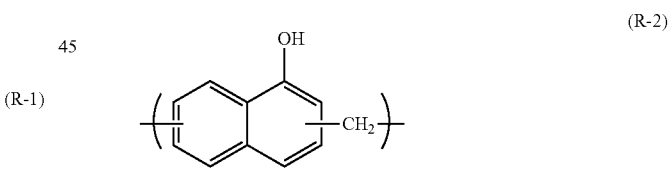

(R-2)

Under a nitrogen atmosphere, 72.0 g of 1-naphthol, 24.3 g of 37% formalin solution, and 250 g of 2-methoxy-1-propanol were mixed to homogeneous solution at a temperature of 80° C. Then, 18 g of 20% 2-methoxy-1-propanol solution of para-toluenesulfonic acid were slowly added and stirred at a temperature of 110° C. for 12 hours. After being cooled to room temperature, 500 g of methyl isobutyl ketone was added, and the organic layer was washed with 200 g of pure water for 5 times followed by drying the organic layer under reduced pressure. To the residue, 300 ml of THF was added, and a polymer was re-precipitated from 2,000 ml of hexane. The precipitated polymer was separated by filtration and dried under reduced pressure to give Compound (R-2).

The weight average molecular weight (Mw) and the degree of dispersion (Mw/Mn) were measured by GPC to give following results:
(R-2): Mw=1800, Mw/Mn=3.33

[Comparative Synthesis Example 3] Synthesis of Compound (R-3)

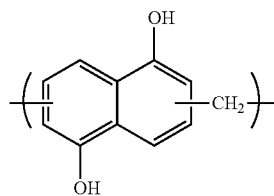

(R-3)

Under a nitrogen atmosphere, 80.1 g of 1,5-dihydroxynaphthalene, 26.4 g of 37% formalin solution, and 250 g of 2-methoxy-1-propanol were mixed to homogeneous solution at a temperature of 80° C. Then, 18 g of 20% 2-methoxy-1-propanol solution of para-toluenesulfonic acid were slowly added and stirred at a temperature of 110° C. for 12 hours. After being cooled to room temperature, 500 g of methyl isobutyl ketone was added, and the organic layer was washed with 200 g of pure water for 5 times followed by drying the organic layer under reduced pressure. To the residue, 300 ml of THF was added, and a polymer was re-precipitated from 2,000 ml of hexane. The precipitated polymer was separated by filtration and dried under reduced pressure to give Compound (R-3).

The weight average molecular weight (Mw) and the degree of dispersion (Mw/Mn) were measured by GPC to give following results:

(R-3): Mw=3000, Mw/Mn=2.65

Preparation of Organic Film Compositions (UDL-1 to 24, Comparative UDL-1 to 3)

In a solvent containing 0.1% by mass of FC-4430 (product of Sumitomo 3M Limited), the foregoing compounds (A-1) to (A-19) and (R-1) to (R-3), a cross-linking agent (CR-1), an acid generator (AG-1) and solvent were dissolved with a ratio shown in Table 5, and then filtered through a 0.1 μm filter made of fluorine resin to prepare each organic film composition (UDL-1 to 24, Comparative UDL-1 to 3).

TABLE 5

| Organic film composition | Compound (1) (parts by mass) | Compound (2) (parts by mass) | Cross-linking agent (parts by mass) | Acid generator (parts by mass) | Solvent (parts by mass) |
|---|---|---|---|---|---|
| UDL-1 | A-1 (10) | | CR-1 (2) | AG-1 (0.5) | PGMEA (90) |
| UDL-2 | A-2 (10) | | CR-1 (2) | AG-1 (0.5) | PGMEA (90) |
| UDL-3 | A-3 (10) | | CR-1 (2) | AG-1 (0.5) | PGMEA (90) |
| UDL-4 | A-4 (10) | | CR-1 (2) | AG-1 (0.5) | PGMEA (90) |
| UDL-5 | A-5 (10) | | CR-1 (2) | AG-1 (0.5) | PGMEA (90) |
| UDL-6 | A-6 (10) | | CR-1 (2) | AG-1 (0.5) | PGMEA (90) |
| UDL-7 | A-7 (10) | | CR-1 (2) | AG-1 (0.5) | PGMEA (90) |
| UDL-8 | A-8 (10) | | CR-1 (2) | AG-1 (0.5) | PGMEA (90) |
| UDL-9 | A-9 (10) | | CR-1 (2) | AG-1 (0.5) | PGMEA (90) |
| UDL-10 | A-10 (10) | | CR-1 (2) | AG-1 (0.5) | PGMEA (90) |
| UDL-11 | A-11 (10) | | CR-1 (2) | AG-1 (0.5) | PGMEA (90) |
| UDL-12 | A-12 (10) | | CR-1 (2) | AG-1 (0.5) | PGMEA (90) |
| UDL-13 | A-13 (10) | | CR-1 (2) | AG-1 (0.5) | PGMEA (90) |
| UDL-14 | A-14 (10) | | CR-1 (2) | AG-1 (0.5) | PGMEA (90) |
| UDL-15 | A-15 (10) | | CR-1 (2) | AG-1 (0.5) | PGMEA (90) |
| UDL-16 | A-16 (10) | | CR-1 (2) | AG-1 (0.5) | PGMEA (90) |
| UDL-17 | A-17 (10) | | CR-1 (2) | AG-1 (0.5) | PGMEA (90) |
| UDL-18 | A-18 (10) | | CR-1 (2) | AG-1 (0.5) | PGMEA (90) |
| UDL-19 | A-19 (10) | | CR-1 (2) | AG-1 (0.5) | PGMEA (90) |
| UDL-20 | A-7 (5) | A-16 (5) | CR-1 (2) | AG-1 (0.5) | PGMEA (90) |
| UDL-21 | A-7 (5) | A-18 (5) | | | PGMEA (90) |
| UDL-22 | A-11 (10) | | | | PGMEA (90) |
| UDL-23 | A-16 (10) | | | | PGMEA (90) |
| UDL-24 | A-18 (10) | | | | PGMEA (90) |
| Comparative UDL-1 | R-1 (10) | | CR-1 (2) | AG-1 (0.5) | PGMEA (90) |
| Comparative UDL-2 | R-2 (10) | | CR-1 (2) | AG-1 (0.5) | PGMEA (90) |
| Comparative UDL-3 | R-3 (10) | | CR-1 (2) | AG-1 (0.5) | PGMEA (90) |

PGMEA: propylene glycol monomethyl ether acetate

The cross-linking agent (CR-1) and the acid generator (AG-1) are shown below.

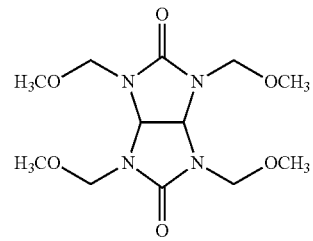

(CR-1)

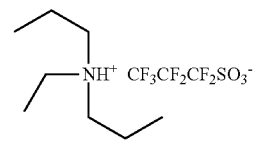

(AG-1)

Measurement of Solvent Resistance (Examples 1-1 to 1-24, Comparative Examples 1-1 to 1-3)

A silicon substrate is coated with each of the organic film compositions prepared above (UDL-1 to 24, Comparative UDL-1 to 3), baked under each condition shown in Table 6, and subsequently, the film thickness was measured. Then, a PGMEA solvent was dispensed thereon, allowed to stand for 30 seconds and spin dried, and baked at 100° C. for 60 seconds to evaporate the PGMEA. Subsequently, the film thickness was measured again to obtain a difference in the film thickness before and after the PGMEA treatment. On the formed organic films (resist under layer films), refractive indexes (n, k) at a wavelength of 193 nm were measured with an incident-angle variable spectroscopic ellipsometer (VASE) manufactured by J. A. Woollam Co., Inc. The results are shown in Table 6.

| Chamber pressure | 40.0 Pa |
| --- | --- |
| RF power | 1,300 W |
| $CHF_3$ gas flow rate | 30 ml/min |
| $CF_4$ gas flow rate | 30 ml/min |
| Ar gas flow rate | 100 ml/min |
| Time | 60 sec |

TABLE 6

| | Organic film composition | Film thickness after film formation: a (Å) | Film thickness after PGMEA treatment: b (Å) | b/a × 100 (%) | Baking temperature | Optical property (193 nm) n value | k value |
| --- | --- | --- | --- | --- | --- | --- | --- |
| Example 1-1 | UDL-1 | 2340 | 2341 | 100.0 | 250° C. × 60 sec | 1.47 | 0.60 |
| Example 1-2 | UDL-2 | 2540 | 2540 | 100.0 | 250° C. × 60 sec | 1.54 | 0.58 |
| Example 1-3 | UDL-3 | 2387 | 2388 | 100.0 | 250° C. × 60 sec | 1.49 | 0.63 |
| Example 1-4 | UDL-4 | 2431 | 2429 | 99.9 | 250° C. × 60 sec | 1.39 | 0.65 |
| Example 1-5 | UDL-5 | 2465 | 2464 | 100.0 | 250° C. × 60 sec | 1.43 | 0.70 |
| Example 1-6 | UDL-6 | 2438 | 2436 | 99.9 | 250° C. × 60 sec | 1.44 | 0.38 |
| Example 1-7 | UDL-7 | 2476 | 2477 | 100.0 | 250° C. × 60 sec | 1.41 | 0.24 |
| Example 1-8 | UDL-8 | 2368 | 2368 | 100.0 | 250° C. × 60 sec | 1.43 | 0.24 |
| Example 1-9 | UDL-9 | 2531 | 2528 | 99.9 | 250° C. × 60 sec | 1.48 | 0.20 |
| Example 1-10 | UDL-10 | 2467 | 2470 | 100.1 | 250° C. × 60 sec | 1.46 | 0.21 |
| Example 1-11 | UDL-11 | 2658 | 2656 | 99.9 | 250° C. × 60 sec | 1.41 | 0.24 |
| Example 1-12 | UDL-12 | 2595 | 2593 | 99.9 | 250° C. × 60 sec | 1.44 | 0.20 |
| Example 1-13 | UDL-13 | 2564 | 2565 | 100.0 | 250° C. × 60 sec | 1.45 | 0.27 |
| Example 1-14 | UDL-14 | 2431 | 2429 | 99.9 | 250° C. × 60 sec | 1.42 | 0.39 |
| Example 1-15 | UDL-15 | 2500 | 2498 | 99.9 | 250° C. × 60 sec | 1.36 | 0.36 |
| Example 1-16 | UDL-16 | 2487 | 2486 | 100.0 | 250° C. × 60 sec | 1.41 | 0.24 |
| Example 1-17 | UDL-17 | 2547 | 2548 | 100.0 | 250° C. × 60 sec | 1.46 | 0.48 |
| Example 1-18 | UDL-18 | 2439 | 2436 | 99.9 | 250° C. × 60 sec | 1.41 | 0.24 |
| Example 1-19 | UDL-19 | 2429 | 2427 | 99.9 | 250° C. × 60 sec | 1.47 | 0.20 |
| Example 1-20 | UDL-20 | 2637 | 2636 | 100.0 | 250° C. × 60 sec | 1.45 | 0.23 |
| Example 1-21 | UDL-21 | 2489 | 2486 | 99.9 | 350° C. × 60 sec | 1.44 | 0.25 |
| Example 1-22 | UDL-22 | 2468 | 2467 | 100.0 | 350° C. × 60 sec | 1.41 | 0.23 |
| Example 1-23 | UDL-23 | 2523 | 2521 | 99.9 | 350° C. × 60 sec | 1.36 | 0.36 |
| Example 1-24 | UDL-24 | 2567 | 2564 | 99.9 | 350° C. × 60 sec | 1.41 | 0.24 |
| Comparative Example 1-1 | Comparative UDL-1 | 2656 | 2656 | 100.0 | 250° C. × 60 sec | 1.35 | 0.72 |
| Comparative Example 1-2 | Comparative UDL-2 | 2830 | 2828 | 99.9 | 250° C. × 60 sec | 1.40 | 0.37 |
| Comparative Example 1-3 | Comparative UDL-3 | 2756 | 2755 | 100.0 | 250° C. × 60 sec | 1.44 | 0.42 |

As shown by Examples 1-1 to 1-24 in Table 6, when using the inventive organic film composition, the film formability were excellent (mirror surface state) in each baking temperature; there were substantially no decrease in each film thickness through the solvent treatment, and it has found that films with excellent solvent resistance were obtained. Particularly, when the organic film compositions containing compounds having naphthalene ring structure such as in Examples 1-21 to 1-24 were used, films with excellent solvent resistance were obtained without any problem of film formability at even 350° C.

As also shown in Table 6, in Examples 1-1 to 1-24, it was found that each organic film showed refractive index in the range of n value of 1.3 to 1.6 and k value of 0.2 to 0.7, and had appropriate refractive index (n) and extinction coefficient (k) to exhibit sufficient antireflection effect.

Etching Test in $CF_4/CHF_3$-Based Gas (Examples 2-1 to 2-24, Comparative Examples 2-1 to 2-3)

The organic films were formed in the same manner as mentioned above, and an etching test with a $CF_4/CHF_3$-based gas was carried out under the following conditions.
Etching Conditions By using an etching apparatus TE-8500 manufactured by Tokyo Electron Limited, the remained films before and after etching were measured. The results are shown in Table 7.

TABLE 7

| | Organic film composition | Film thickness before etching: a (Å) | Film thickness after etching: b (Å) | b/a × 100 (%) | Baking temperature |
| --- | --- | --- | --- | --- | --- |
| Example 2-1 | UDL-1 | 2340 | 1103 | 47.1 | 250° C. × 60 sec |
| Example 2-2 | UDL-2 | 2540 | 1203 | 47.4 | 250° C. × 60 sec |
| Example 2-3 | UDL-3 | 2387 | 1135 | 47.5 | 250° C. × 60 sec |
| Example 2-4 | UDL-4 | 2431 | 1203 | 49.5 | 250° C. × 60 sec |
| Example 2-5 | UDL-5 | 2465 | 1244 | 50.5 | 250° C. × 60 sec |
| Example 2-6 | UDL-6 | 2438 | 1207 | 49.5 | 250° C. × 60 sec |
| Example 2-7 | UDL-7 | 2476 | 1225 | 49.5 | 250° C. × 60 sec |
| Example 2-8 | UDL-8 | 2368 | 1195 | 50.5 | 250° C. × 60 sec |

TABLE 7-continued

| | Organic film composition | Film thickness before etching: a (Å) | Film thickness after etching: b (Å) | b/a × 100 (%) | Baking temperature |
|---|---|---|---|---|---|
| Example 2-9 | UDL-9 | 2531 | 1288 | 50.9 | 250° C. × 60 sec |
| Example 2-10 | UDL-10 | 2467 | 1276 | 51.7 | 250° C. × 60 sec |
| Example 2-11 | UDL-11 | 2658 | 1338 | 50.3 | 250° C. × 60 sec |
| Example 2-12 | UDL-12 | 2595 | 1251 | 48.2 | 250° C. × 60 sec |
| Example 2-13 | UDL-13 | 2564 | 1261 | 49.2 | 250° C. × 60 sec |
| Example 2-14 | UDL-14 | 2431 | 1151 | 47.4 | 250° C. × 60 sec |
| Example 2-15 | UDL-15 | 2500 | 1332 | 53.3 | 250° C. × 60 sec |
| Example 2-16 | UDL-16 | 2487 | 1297 | 52.1 | 250° C. × 60 sec |
| Example 2-17 | UDL-17 | 2547 | 1284 | 50.4 | 250° C. × 60 sec |
| Example 2-18 | UDL-18 | 2439 | 1266 | 51.9 | 250° C. × 60 sec |
| Example 2-19 | UDL-19 | 2429 | 1188 | 48.9 | 250° C. × 60 sec |
| Example 2-20 | UDL-20 | 2637 | 1340 | 50.8 | 250° C. × 60 sec |
| Example 2-21 | UDL-21 | 2489 | 1262 | 50.7 | 350° C. × 60 sec |
| Example 2-22 | UDL-22 | 2468 | 1180 | 47.8 | 350° C. × 60 sec |
| Example 2-23 | UDL-23 | 2523 | 1315 | 52.1 | 350° C. × 60 sec |
| Example 2-24 | UDL-24 | 2567 | 1332 | 51.9 | 350° C. × 60 sec |
| Comparative Example 2-1 | Comparative UDL-1 | 2656 | 1216 | 45.8 | 250° C. × 60 sec |
| Comparative Example 2-2 | Comparative UDL-2 | 2830 | 1494 | 52.8 | 250° C. × 60 sec |
| Comparative Example 2-3 | Comparative UDL-3 | 2756 | 1419 | 51.5 | 250° C. × 60 sec |

As shown in Table 7, it was confirmed that the inventive organic film compositions (UDL-1 to 24) had the same or superior etching resistance to those of the comparative organic film compositions (Comparative UDL-1 to 3).

Evaluation of Filling Property (Examples 3-1 to 3-24, Comparative Examples 3-1 to 3-3)

Figure 2:
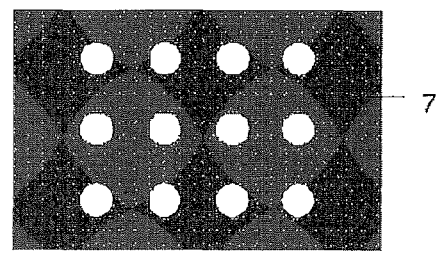
FIG. 2 is an explanatory view of an evaluation method of filling property in Examples and Comparative Examples.
Figure 2:
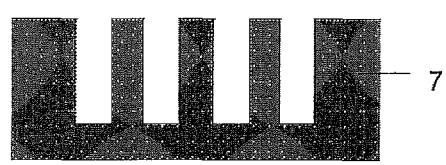
Figure 2:
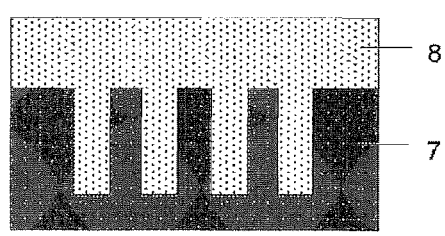

As shown in FIG. 2, each of the foregoing organic film compositions was applied onto a SiO$_2$ wafer substrate having a dense hole pattern (hole diameter: 0.16 µm, hole depth: 0.50 µm, distance between the centers of the adjacent two holes: 0.32 µm), and heated with a hot plate at 150° C. for 60 seconds, to form an organic film 8. The used substrate was a ground substrate 7 (SiO$_2$ wafer substrate) having a dense hole pattern as shown in FIG. 2(G) (downward view) and FIG. 2 (H) (sectional view). The cross-sectional shape of each obtained wafer substrate was observed by using a scanning electron microscope (SEM) to confirm whether inside of the hole was filled by the organic film without voids (vacancies). The results are shown in Table 8. When an organic film composition with inferior filling property is used, voids occur at the inside of the hole in this evaluation. When an organic film compositions with good filling property are employed, the organic film is filled without any voids at the inside of the hole in this evaluation as shown in FIG. 2(I).

TABLE 8

| | Organic film composition | Presence or absence of voids |
|---|---|---|
| Example 3-1 | UDL-1 | None |
| Example 3-2 | UDL-2 | None |
| Example 3-3 | UDL-3 | None |
| Example 3-4 | UDL-4 | None |
| Example 3-5 | UDL-5 | None |
| Example 3-6 | UDL-6 | None |
| Example 3-7 | UDL-7 | None |
| Example 3-8 | UDL-8 | None |
| Example 3-9 | UDL-9 | None |
| Example 3-10 | UDL-10 | None |
| Example 3-11 | UDL-11 | None |
| Example 3-12 | UDL-12 | None |
| Example 3-13 | UDL-13 | None |
| Example 3-14 | UDL-14 | None |
| Example 3-15 | UDL-15 | None |
| Example 3-16 | UDL-16 | None |
| Example 3-17 | UDL-17 | None |
| Example 3-18 | UDL-18 | None |
| Example 3-19 | UDL-19 | None |
| Example 3-20 | UDL-20 | None |
| Example 3-21 | UDL-21 | None |
| Example 3-22 | UDL-22 | None |
| Example 3-23 | UDL-23 | None |
| Example 3-24 | UDL-24 | None |
| Comparative Example 3-1 | Comparative UDL-1 | Present |
| Comparative Example 3-2 | Comparative UDL-2 | Present |
| Comparative Example 3-3 | Comparative UDL-3 | Present |

As shown in Table 8, it was confirmed that the inventive organic film compositions (UDL-1 to 24) can fill the hole pattern without any voids, and have excellent filling property as compared with those of the comparative organic compositions (Comparative UDL-1 to 3). In particular, comparing Examples 3-6 to 3-24 (UDL-6 to 24) and Comparative Examples 3-2 and 3-3 (Comparative UDL-2 and 3), voids appeared in Comparative Examples 3-2 and 3-3, in which novolac resins with naphthalene ring structures were used, on the other hand, the inventive organic film composition could fill the hole pattern even though each of them had a naphthalene ring structure. This also shows the superiority of filling property of the inventive organic film composition.

Evaluation of Planarizing Characteristics (Examples 4-1 to 4-24, Comparative Examples 4-1 to 4-3)

Figure 3:
FIG. 3 is an explanatory view of an evaluation method of planarizing characteristics in Examples and Comparative Examples.
Figure 3:
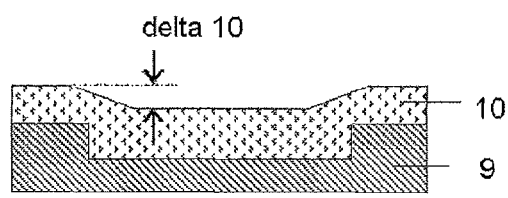

The foregoing organic film compositions were each applied onto a ground substrate 9 (SiO$_2$ wafer substrate) having a giant isolated trench pattern (FIG. 3(J), trench width: 10 µm, trench depth: 0.50 µm), and after baking the composition under the conditions shown in Table 9, a difference in film thicknesses at the trench portion and the non-trench portion of the organic film (delta 10 in FIG. 3(K)) was observed with a scanning electron microscope (SEM). The results are shown in Table 9. In this evaluation, as the difference between the film thicknesses is small, planarizing characteristics can be said to be good. Incidentally, in this evaluation, the trench pattern having a depth of 0.50 µm was planarized by using an organic film composition having a usual film thickness of about 0.3 µm, which is a specific severe evaluation condition to evaluate superiority or inferiority of the planarizing.

TABLE 9

| | Organic film composition | Baking temperature | Difference in film thicknesses (nm) |
|---|---|---|---|
| Example 4-1 | UDL-1 | 250° C. × 60 sec | 35 |
| Example 4-2 | UDL-2 | 250° C. × 60 sec | 40 |
| Example 4-3 | UDL-3 | 250° C. × 60 sec | 35 |
| Example 4-4 | UDL-4 | 250° C. × 60 sec | 35 |
| Example 4-5 | UDL-5 | 250° C. × 60 sec | 40 |
| Example 4-6 | UDL-6 | 250° C. × 60 sec | 35 |
| Example 4-7 | UDL-7 | 250° C. × 60 sec | 35 |
| Example 4-8 | UDL-8 | 250° C. × 60 sec | 35 |
| Example 4-9 | UDL-9 | 250° C. × 60 sec | 30 |
| Example 4-10 | UDL-10 | 250° C. × 60 sec | 30 |
| Example 4-11 | UDL-11 | 250° C. × 60 sec | 45 |
| Example 4-12 | UDL-12 | 250° C. × 60 sec | 30 |
| Example 4-13 | UDL-13 | 250° C. × 60 sec | 35 |
| Example 4-14 | UDL-14 | 250° C. × 60 sec | 35 |
| Example 4-15 | UDL-15 | 250° C. × 60 sec | 40 |
| Example 4-16 | UDL-16 | 250° C. × 60 sec | 40 |
| Example 4-17 | UDL-17 | 250° C. × 60 sec | 40 |
| Example 4-18 | UDL-18 | 250° C. × 60 sec | 40 |
| Example 4-19 | UDL-19 | 250° C. × 60 sec | 30 |
| Example 4-20 | UDL-20 | 250° C. × 60 sec | 40 |
| Example 4-21 | UDL-21 | 350° C. × 60 sec | 40 |
| Example 4-22 | UDL-22 | 350° C. × 60 sec | 30 |
| Example 4-23 | UDL-23 | 350° C. × 60 sec | 35 |
| Example 4-24 | UDL-24 | 350° C. × 60 sec | 30 |
| Comparative Example 4-1 | Comparative UDL-1 | 250° C. × 60 sec | 90 |
| Comparative Example 4-2 | Comparative UDL-2 | 250° C. × 60 sec | 90 |
| Comparative Example 4-3 | Comparative UDL-3 | 250° C. × 60 sec | 100 |

As shown in Table 9, each of the inventive organic film compositions (UDL-1 to 24) showed smaller difference in film thicknesses of the organic film at the trench portion and at the non-trench portion, as compared with those of the comparative organic film compositions (Comparative UDL-1 to 3), and are confirmed to show the superiority of planarizing characteristic. Particularly, it was found that in Examples 4-9, 4-10, 4-12 to 4-14, and 4-19 using each compound synthesized by combining an aliphatic carboxylic acid compound and an aromatic carboxylic acid compound, the planarizing characteristic is improved as compared to Examples 4-7, 4-11, 4-17, and 4-18 using each compound synthesized by the corresponding epoxy compound and an aromatic carboxylic acid compound alone.

Pattern Formation Test (Examples 5-1 to 5-24)

The organic film compositions (UDL-1 to 24) were each applied onto a SiO$_2$ wafer substrate having a trench pattern (trench width: 10 μm, trench depth: 0.10 μm), and baked by the condition described in Table 12 to prepare an organic film (resist under layer film). The resist middle layer film composition SOG1 was applied thereon and baked at 200° C. for 60 seconds to form a resist middle layer film having a film thickness of 35 nm, and a single layer resist for ArF of a resist upper layer film composition was applied thereon and baked at 105° C. for 60 seconds to form a photoresist film having a film thickness of 100 nm. The liquid immersion protective film material (TC-1) was applied onto the photoresist film, and baked at 90° C. for 60 seconds to form a protective film having a film thickness of 50 nm.

As the resist middle layer film composition (SOG-1), 2% propylene glycol ethyl ether solution of the following polymer was prepared.

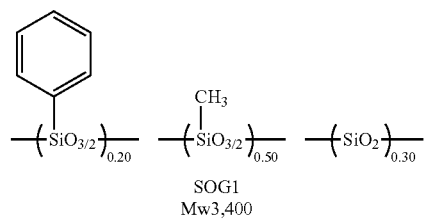

SOG1
Mw3,400

In a solvent containing 0.1% by mass of FC-430 (product of Sumitomo 3M Limited), a polymer (RP1), an acid generator (PAG1), and a basic compound (Amine 1) were dissolved with a ratio shown in Table 10, and then filtered through a 0.1 μm filter made of fluorine resin to prepare a resist upper layer film composition (single layer resist for ArF).

TABLE 10

| No. | Polymer (parts by mass) | Acid generator (parts by mass) | Basic compound (part by mass) | Solvent (parts by mass) |
|---|---|---|---|---|
| Single layer resist for ArF | RP1 (100) | PAG1 (6.6) | Amine 1 (0.8) | PGMEA (2,500) |

The polymer (RP1), the acid generator (PAG1), and the basic compound (Amine 1) used in the Examples are shown below.

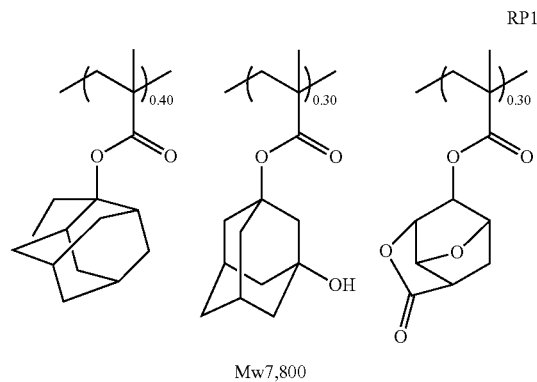

RP1

Mw7,800

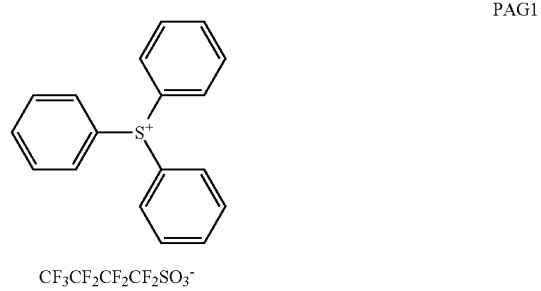

PAG1

-continued

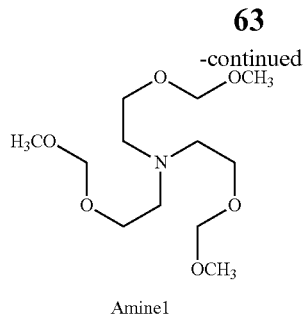

Amine1

As a liquid immersion protective film material (TC-1), the polymer (PP1) was dissolved in an organic solvent with a ratio shown in Table 11, and then filtered through a 0.1 μm filter made of a fluorine resin to prepare the material.

TABLE 11

| | Polymer (parts by mass) | Organic solvent (parts by mass) |
|---|---|---|
| TC-1 | PP1 (100) | Diisoamyl ether (2,700) 2-methyl-1-butanol (270) |

The used polymer (PP1) is shown below.

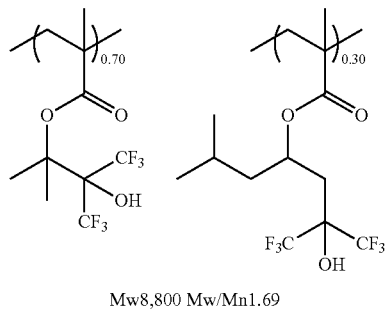

Mw8,800 Mw/Mn1.69

Then, the coated substrate was exposed by using ArF liquid immersion exposure apparatus (product of Nikon Corporation: NSR-S610C, NA 1.30, σ 0.98/0.65, 35° dipole s polarized illumination, 6% half-tone phase shift mask), baked at 100° C. for 60 seconds (PEB), and developed by 2.38% by mass aqueous tetramethylammonium hydroxide (TMAH) solution for 30 seconds, to obtain 55 nm 1:1 positive-type line-and-space pattern.

Subsequently, the resist middle layer film was subjected to etching processing by using the resist pattern as a mask by dry etching using an etching apparatus Telius manufactured by Tokyo Electron Limited to form a resist middle layer film pattern, the resist under layer film was subjected to etching by using the obtained resist middle layer film pattern as a mask to form a resist under layer film pattern, and the $SiO_2$ film was subjected to etching processing by using the obtained resist under layer film pattern as a mask. The etching conditions are as shown below.

Transcription conditions of the resist pattern to the resist middle layer film.

| Chamber pressure | 10.0 Pa |
|---|---|
| RF power | 1,500 W |
| $CF_4$ gas flow rate | 75 sccm |

| $O_2$ gas flow rate | 15 sccm |
|---|---|
| Time | 15 sec |

Transcription conditions of the resist middle layer film pattern to the resist under layer film.

| Chamber pressure | 2.0 Pa |
|---|---|
| RF power | 500 W |
| Ar gas flow rate | 75 sccm |
| $O_2$ gas flow rate | 45 sccm |
| Time | 120 sec |

Transcription conditions of the resist under layer film pattern to the $SiO_2$ film.

| Chamber pressure | 2.0 Pa |
|---|---|
| RF power | 2,200 W |
| $C_5F_{12}$ gas flow rate | 20 sccm |
| $C_2F_6$ gas flow rate | 10 sccm |
| Ar gas flow rate | 300 sccm |
| $O_2$ | 60 sccm |
| Time | 90 sec |

The pattern cross-section was observed with an electron microscope (S-4700) manufactured by Hitachi, Ltd., and the results are shown in Table 12.

TABLE 12

| | Organic film composition | Baking temperature | Pattern shape after substrate transcription and etching |
|---|---|---|---|
| Example 5-1 | UDL-1 | 250° C. × 60 sec | Perpendicular shape |
| Example 5-2 | UDL-2 | 250° C. × 60 sec | Perpendicular shape |
| Example 5-3 | UDL-3 | 250° C. × 60 sec | Perpendicular shape |
| Example 5-4 | UDL-4 | 250° C. × 60 sec | Perpendicular shape |
| Example 5-5 | UDL-5 | 250° C. × 60 sec | Perpendicular shape |
| Example 5-6 | UDL-6 | 250° C. × 60 sec | Perpendicular shape |
| Example 5-7 | UDL-7 | 250° C. × 60 sec | Perpendicular shape |
| Example 5-8 | UDL-8 | 250° C. × 60 sec | Perpendicular shape |
| Example 5-9 | UDL-9 | 250° C. × 60 sec | Perpendicular shape |
| Example 5-10 | UDL-10 | 250° C. × 60 sec | Perpendicular shape |
| Example 5-11 | UDL-11 | 250° C. × 60 sec | Perpendicular shape |
| Example 5-12 | UDL-12 | 250° C. × 60 sec | Perpendicular shape |
| Example 5-13 | UDL-13 | 250° C. × 60 sec | Perpendicular shape |
| Example 5-14 | UDL-14 | 250° C. × 60 sec | Perpendicular shape |
| Example 5-15 | UDL-15 | 250° C. × 60 sec | Perpendicular shape |
| Example 5-16 | UDL-16 | 250° C. × 60 sec | Perpendicular shape |
| Example 5-17 | UDL-17 | 250° C. × 60 sec | Perpendicular shape |
| Example 5-18 | UDL-18 | 250° C. × 60 sec | Perpendicular shape |
| Example 5-19 | UDL-19 | 250° C. × 60 sec | Perpendicular shape |
| Example 5-20 | UDL-20 | 250° C. × 60 sec | Perpendicular shape |
| Example 5-21 | UDL-21 | 350° C. × 60 sec | Perpendicular shape |
| Example 5-22 | UDL-22 | 350° C. × 60 sec | Perpendicular shape |
| Example 5-23 | UDL-23 | 350° C. × 60 sec | Perpendicular shape |
| Example 5-24 | UDL-24 | 350° C. × 60 sec | Perpendicular shape |

As shown in Table 12, in each Example according to the present invention, resist upper layer film pattern was finally transferred to the substrate favorably. It was confirmed that the inventive organic film composition can be suitably used for fine processing by the multilayer resist process, even on a substrate having a step(s).

It is to be noted that the present invention is not limited to the foregoing embodiment. The embodiment is just an exemplification, and any examples that have substantially the same feature and demonstrate the same functions and effects as those in the technical concept described in claims of the present invention are included in the technical scope of the present invention.

What is claimed is:

1. An organic film composition comprising a compound represented by the following general formula (4),

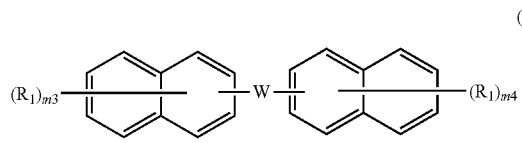
(4)

wherein m3 and m4 each independently represent 1 or 2; "W" represents a single bond or any of structures represented by the following formula (2); $R_1$ represents any of structures represented by the following general formula (3);

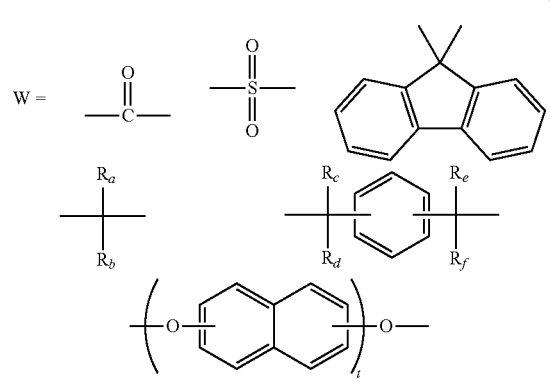
(2)

wherein "t" represents an integer of 0 to 3; $R_a$ to $R_f$ each independently represent a hydrogen atom, or an alkyl group having 1 to 10 carbon atoms, a phenyl group, or a phenylethyl group which may be substituted by a fluorine atom, and $R_a$ and $R_b$ may be bonded to each other to form a ring compound;

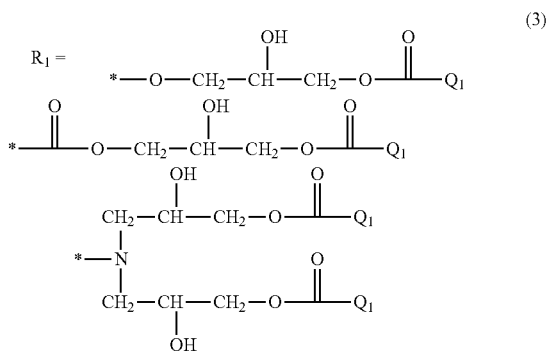
(3)

wherein "*" represents a bonding site to the aromatic ring; $Q_1$ represents a linear or branched saturated hydrocarbon group having 1 to 30 carbon atoms, an alicyclic group having 4 to 20 carbon atoms, or a substituted or unsubstituted phenyl group, naphthyl group, anthracenyl group, or pyrenyl group, and the methylene group constituting $Q_1$ may be substituted by an oxygen atom or a carbonyl group when $Q_1$ represents a linear or branched saturated hydrocarbon group having 1 to 30 carbon atoms.

2. The organic film composition according to claim 1, wherein "W" represents a single bond or any of structures represented by the following formula (5),

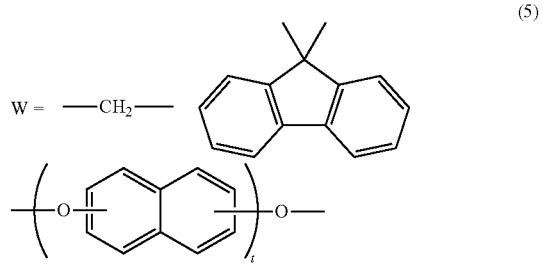
(5)

wherein "t" has the same meaning as defined above.

3. The organic film composition according to claim 2, the compound represented by the general formula (4) has two or more $Q_1$ in the molecule, and contains one or more structures represented by the following general formula (6) and one or more structures represented by the following general formula (7) respectively as $Q_1$,

(6)

wherein "**" represents a bonding site to the carbonyl group; $R_h$ represents a linear or branched saturated hydrocarbon group having 1 to 30 carbon atoms, and the methylene group constituting $R_h$ may be substituted by an oxygen atom or a carbonyl group,

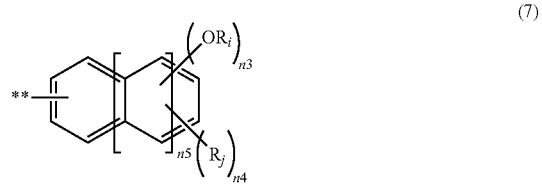
(7)

wherein "**" represents a bonding site to the carbonyl group; $R_i$ represents a hydrogen atom, or a linear or branched hydrocarbon group having 1 to 10 carbon atoms; $R_j$ represents a linear or branched hydrocarbon group having 1 to 10 carbon atoms, a halogen atom, a nitro group, an amino group, a nitrile group, an alkoxycarbonyl group having 1 to 10 carbon atoms, or an alkanoyloxy group having 1 to 10 carbon atoms; n3 and n4 represent the numbers of substituents on the aromatic ring, and each represent an integer of 0 to 7, with the proviso that n3+n4 is 0 to 7; n5 represents 0 to 2.

4. The organic film composition according to claim 1, the compound represented by the general formula (4) has two or more $Q_1$ in the molecule, and contains one or more structures represented by the following general formula (6) and one or more structures represented by the following general formula (7) respectively as $Q_1$,

(6)

wherein "**" represents a bonding site to the carbonyl group; $R_h$ represents a linear or branched saturated hydrocarbon group having 1 to 30 carbon atoms, and the methylene group constituting $R_h$ may be substituted by an oxygen atom or a carbonyl group,

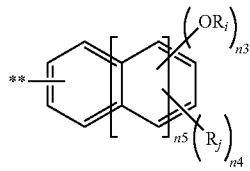
(7)

wherein "**" represents a bonding site to the carbonyl group; $R_i$ represents a hydrogen atom, or a linear or branched hydrocarbon group having 1 to 10 carbon atoms; $R_j$ represents a linear or branched hydrocarbon group having 1 to 10 carbon atoms, a halogen atom, a nitro group, an amino group, a nitrile group, an alkoxycarbonyl group having 1 to 10 carbon atoms, or an alkanoyloxy group having 1 to 10 carbon atoms; n3 and n4 represent the numbers of substituents on the aromatic ring, and each represent an integer of 0 to 7, with the proviso that n3+n4 is 0 to 7; n5 represents 0 to 2.

5. The organic film composition according to claim 1, further comprising at least one of (A) an acid generator, (B) a cross-linking agent, (C) a surfactant, and (D) an organic solvent.

6. A process for forming an organic film which acts as a resist under layer film of a multilayer resist film used in lithography or a planarizing film for manufacturing a semiconductor apparatus, comprising:
coating a substrate to be processed with the organic film composition according to claim 1, and
subjecting the organic film composition to heat treatment at a temperature of 100° C. or higher and 600° C. or lower for 10 to 600 seconds to form a cured film.

7. The process for forming an organic film according to claim 6, wherein the substrate to be processed is a substrate to be processed having a structure or step(s) each with a height of 30 nm or more.

8. A process for forming an organic film which acts as a resist under layer film of a multilayer resist film used in lithography or a planarizing film for manufacturing a semiconductor apparatus, comprising:
coating a substrate to be processed with the organic film composition according to claim 1, and
baking the organic film composition under an atmosphere with an oxygen concentration of 0.1% or more and 21% or less to form a cured film.

9. A patterning process which is a process for forming a pattern on a substrate to be processed, comprising at least the steps of:
forming a resist under layer film on the substrate to be processed by using the organic film composition according to claim 1;
forming a resist middle layer film on the resist under layer film by using a resist middle layer film composition containing a silicon atom;
forming a resist upper layer film on the resist middle layer film by using a resist upper layer film composition comprising a photoresist composition, to form a multilayer resist film;
forming a resist pattern on the resist upper layer film by exposing a pattern circuit region of the resist upper layer film and then developing the same with a developer;
forming a resist middle layer film pattern by etching the resist middle layer film using the obtained resist pattern as an etching mask;
forming a resist under layer film pattern by etching the resist under layer film using the obtained resist middle layer film pattern as an etching mask; and further
forming a pattern on the substrate to be processed by etching the substrate to be processed using the obtained resist under layer film pattern as an etching mask.

10. The patterning process according to claim 9, wherein the step of etching the resist under layer film using the resist middle layer film as an etching mask is performed by using an etching gas mainly comprising an oxygen gas or a hydrogen gas.

11. The patterning process according to claim 9, wherein the substrate to be processed is a substrate to be processed having a structure or step(s) each with a height of 30 nm or more.

12. A patterning process which is a process for forming a pattern on a substrate to be processed, comprising at least the steps of:
forming a resist under layer film on the substrate to be processed by using the organic film composition according to claim 1;
forming an inorganic hard mask middle layer film selected from any one of a silicon oxide film, a silicon nitride film, and a silicon oxynitride film on the resist under layer film;
forming a resist upper layer film on the inorganic hard mask middle layer film by using a resist upper layer film composition comprising a photoresist composition, to form a multilayer resist film;
forming a resist pattern on the resist upper layer film by exposing a pattern circuit region of the resist upper layer film and then developing the same with a developer;
forming an inorganic hard mask middle layer film pattern by etching the inorganic hard mask middle layer film using the obtained resist pattern as an etching mask;
forming a resist under layer film pattern by etching the resist under layer film using the obtained inorganic hard mask middle layer film pattern as an etching mask; and further
forming a pattern on the substrate to be processed by etching the substrate to be processed using the obtained resist under layer film pattern as an etching mask.

13. The patterning process according to claim 12, wherein the inorganic hard mask middle layer film is formed by a CVD method or an ALD method.

14. A patterning process which is a process for forming a pattern on a substrate to be processed, comprising at least the steps of:
forming a resist under layer film on the substrate to be processed by using the organic film composition according to claim 1;
forming an inorganic hard mask middle layer film selected from any one of a silicon oxide film, a silicon nitride film, and a silicon oxynitride film on the resist under layer film;
forming an organic antireflection film on the inorganic hard mask middle layer film;
forming a resist upper layer film on the organic antireflection film by using a resist upper layer film composition comprising a photoresist composition, to form a multilayer resist film;

forming a resist pattern on the resist upper layer film by exposing a pattern circuit region of the resist upper layer film and then developing the same with a developer;

forming an inorganic hard mask middle layer film pattern by etching the organic antireflection film and the inorganic hard mask middle layer film using the obtained resist pattern as an etching mask;

forming a resist under layer film pattern by etching the resist under layer film using the obtained inorganic hard mask middle layer film pattern as an etching mask; and further forming a pattern on the substrate to be processed by etching the substrate to be processed using the obtained resist under layer film pattern as an etching mask.

15. A compound represented by the following general formula (4),

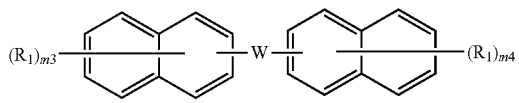
(4)

wherein m3 and m4 each independently represent 1 or 2; "W" represents a single bond or any of structures represented by the following formula (2); $R_1$ represents any of structures represented by the following general formula (3);

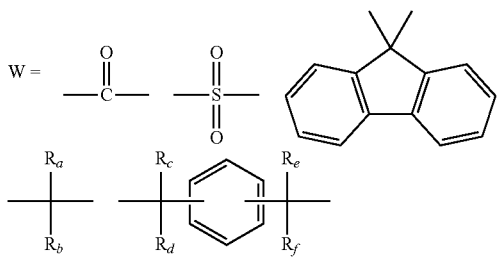
(2)

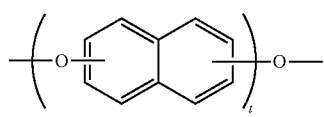

wherein "t" represents an integer of 0 to 3; $R_a$ to $R_f$ each independently represent a hydrogen atom, or an alkyl group having 1 to 10 carbon atoms, a phenyl group, or a phenylethyl group which may be substituted by a fluorine atom, and $R_a$ and $R_b$ may be bonded to each other to form a ring compound;

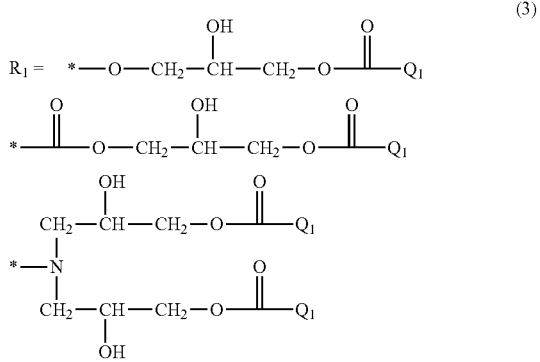
(3)

wherein "*" represents a bonding site to the aromatic ring; $Q_1$ represents a linear or branched saturated hydrocarbon group having 1 to 30 carbon atoms, an alicyclic group having 4 to 20 carbon atoms, or a substituted or unsubstituted phenyl group, naphthyl group, anthracenyl group, or pyrenyl group, and the methylene group constituting $Q_1$ may be substituted by an oxygen atom or a carbonyl group when $Q_1$ represents a linear or branched saturated hydrocarbon group having 1 to 30 carbon atoms.

* * * * *